(12) United States Patent
Feldon et al.

(10) Patent No.: US 6,776,756 B2
(45) Date of Patent: Aug. 17, 2004

(54) APPLANATION TONOMETER

(75) Inventors: Steven E. Feldon, Rochester, NY (US); Bruce Allen Burr, Tustin, CA (US); Richard Wademan Teasdale, Torrey, UT (US); Gregory John Netherwood, Orange, CA (US)

(73) Assignee: Marco Ophthalmic, Inc., Jacksonville, FL (US)

( * ) Notice: Subject to any disclaimer, the term of this patent is extended or adjusted under 35 U.S.C. 154(b) by 0 days.

(21) Appl. No.: 10/137,234

(22) Filed: Apr. 30, 2002

(65) Prior Publication Data

US 2002/0173712 A1 Nov. 21, 2002

Related U.S. Application Data

(60) Provisional application No. 60/293,021, filed on May 15, 2001.

(51) Int. Cl.[7] .................................................. A61B 3/16
(52) U.S. Cl. ....................................... 600/405; 600/406
(58) Field of Search ................................ 600/398, 399, 600/405, 406, 561, 587; 428/426, 428, 330; 359/599

(56) References Cited

U.S. PATENT DOCUMENTS

| | | | |
|---|---|---|---|
| 1,331,777 A | | 2/1920 | Many |
| 2,157,293 A | * | 5/1939 | Lenta ............................... 2/21 |
| 3,049,001 A | | 8/1962 | Mackay et al. |
| 3,070,997 A | | 1/1963 | Papritz et al. |
| 3,150,520 A | | 9/1964 | Mackay et al. |
| 3,150,521 A | | 9/1964 | Mackay et al. |
| 3,272,001 A | | 9/1966 | Adise |
| 3,287,957 A | | 11/1966 | Martens |
| 3,338,089 A | | 8/1967 | Coombs et al. |
| 3,338,090 A | * | 8/1967 | Coombs, Jr. et al. ....... 600/405 |
| 3,390,572 A | | 7/1968 | Murr |
| 3,446,061 A | | 5/1969 | Draeger et al. |
| 3,449,945 A | | 6/1969 | Mohrman |
| 3,449,946 A | | 6/1969 | Gabriel et al. |

(List continued on next page.)

FOREIGN PATENT DOCUMENTS

DE 3421701 A1 * 12/1984 ............ A61B/3/16

*Primary Examiner*—Eric F. Winakur
*Assistant Examiner*—David J. McCrosky
(74) *Attorney, Agent, or Firm*—Orrick, Herrington & Sutcliffe, LLP

(57) ABSTRACT

For calculating the intraocular pressure (IOP) of an eye, an applanation tonometer comprises an applanator formed of an optics array, a force transducer, an image sensor, and a processing circuit configured to calculate an intraocular pressure of the eye using one or more pairs of measured force and applanated area. The tonometer is provided with a disposable tip that covers the applanator, thereby providing a replaceable, sterile and transmissive interface between the tonometer's applanator and a patient's eye. Preferably, the applanating surface has a matte finish. The tonometer calculates the intraocular pressure using a predetermined relationship between interocular pressure and the slope of the line defined by data relating to the forces required to applanate the eye and the geometry of applanated portions of the eye. In a preferred embodiment, the data acquisition is synchronous. The tonometer may be of the type of a portable, hand-held device or a device affixed to and used in conjunction with a slit-lamp design. Also disclosed is a method and device for applying a disposable tip to the applanator.

33 Claims, 22 Drawing Sheets

U.S. PATENT DOCUMENTS

| | | |
|---|---|---|
| 3,487,679 A | 1/1970 | Yamamori |
| 3,511,085 A | 5/1970 | Posner et al. |
| 3,913,390 A * | 10/1975 | Piazza .................. 600/405 |
| 3,977,237 A | 8/1976 | Tesi |
| 4,192,317 A | 3/1980 | Munnerlyn et al. |
| 4,213,464 A | 7/1980 | Katz et al. |
| 4,523,597 A | 6/1985 | Sawa et al. |
| 4,621,644 A | 11/1986 | Eilers |
| 4,622,459 A | 11/1986 | Bouge et al. |
| 4,624,235 A | 11/1986 | Krabacher et al. |
| 4,747,296 A | 5/1988 | Feldon et al. |
| 4,759,370 A | 7/1988 | Kozin et al. |
| 4,766,904 A | 8/1988 | Kozin et al. |
| 4,860,755 A | 8/1989 | Erath |
| 4,922,914 A | 5/1990 | Segal et al. |
| 4,987,899 A | 1/1991 | Brown |
| 5,002,057 A | 3/1991 | Brady |
| 5,031,622 A | 7/1991 | LaHaye |
| 5,056,522 A | 10/1991 | Matsumura et al. |
| 5,070,875 A | 12/1991 | Falck et al. |
| 5,113,863 A | 5/1992 | Herman |
| 5,165,409 A | 11/1992 | Coan |
| 5,174,292 A | 12/1992 | Kursar |
| 5,203,331 A | 4/1993 | Draeger |
| 5,282,470 A | 2/1994 | Cohen et al. |
| 5,284,149 A | 2/1994 | Dhadwal et al. |
| 5,305,747 A | 4/1994 | McNaughton et al. |
| 5,318,029 A | 6/1994 | Palese |
| 5,355,884 A | 10/1994 | Bennett |
| 5,363,855 A | 11/1994 | Drzewiecki et al. |
| 5,546,941 A | 8/1996 | Zeimer et al. |
| 5,671,737 A | 9/1997 | Harosi |
| 5,830,139 A | 11/1998 | Abreu |
| 5,954,646 A | 9/1999 | Jost et al. |
| 6,045,503 A | 4/2000 | Grabner et al. |
| 6,083,160 A | 7/2000 | Lipman |
| 6,093,147 A | 7/2000 | Kontiola |
| 6,110,110 A | 8/2000 | Dublin et al. |
| 6,123,668 A | 9/2000 | Abreu |
| 6,131,574 A | 10/2000 | Kohayakawa |
| 6,179,779 B1 | 1/2001 | Falck et al. |

* cited by examiner

EYESOPEN HIGHLEVEL
FLOW DIAGRAM

WAITING FOR
READINGPROCESS

TAKE READINGS
PROCESS

CANDIDATE DIAMETER

APPLANATION TONOMETER

The present application is related to U.S. provisional patent application serial No. 60/293,021, filed May 15, 2001, the contents of which are fully incorporated herein by reference.

BACKGROUND OF THE INVENTION

The invention relates to the measurement of intraocular pressure and, in particular, to methods and apparati for measuring intraocular pressure using applanation tonometry.

The measurement of intraocular pressure (IOP) is essential to the diagnosis and management of glaucoma, a major cause of blindness in the United States and around the world. Although direct measurement of intraocular pressure can be obtained by inserting a pressure sensitive probe into the eye, clinical methods must rely on indirect methods of obtaining intraocular pressure. There are two popular methods for obtaining these indirect measurements. In a first method, the eye is indented using a tonometer, popularized by Schiotz, wherein gram weights are placed on a central post that exerts pressure on a globe relative to a curved plate that covers an anesthetized cornea. This method has several disadvantages, which include the requirement that the patient remain in a supine position in addition to errors in measurement related to scleral rigidity. Also, the Schiotz tonometer requires a normogram to interpret the measured pressure.

The second method for obtaining an indirect measurement of intraocular pressure is the applanation technique, wherein a portion of the cornea is flattened by a mechanical device. In applanation techniques, the force required to produce a flattening of the cornea is related to intraocular pressure, so the intraocular pressure can be determined indirectly by measuring the flattening of the cornea and the pressure required to produce that flattening. Goldmann determined the exact area required such that one gram of force is equivalent to one mm Hg of intraocular pressure. McKay and Marg developed an electronic tonometer based on differential applanation between a central post and a surrounding annulus. This principle is utilized by the TONO-PEN™ electronic tonometer, patented by Feldon et al. in U.S. Pat. No. 4,747,296. A variant of the applanation methodology requires no direct contact with the patient's eye. This "air puff" technique involves directing a calibrated packet of pressurized air onto the corneal surface, which causes corneal flattening. This corneal flattening is then measured indirectly by measuring the deflection of light reflected from the corneal surface.

Of the various types of tonometers available for clinical use, the Goldmann applanation tonometer is considered the "gold standard." However, there are several shortcomings to this technique. First, the device, as originally designed, is not portable, but is attached to a slit lamp. This issue has been addressed by the Perkins and Kowa tonometers that incorporate a Goldmann-type tonometer in a portable design. Second, these tonometers are manual devices that rely upon a highly trained observer to obtain reliable results. Third, the prolonged amount of time required to position the patient as well as poor patient tolerance make Goldmann tonometry inefficient and sometimes impossible to perform. Finally, a Goldmann tonometer touches the eye with a non-disposable device that is difficult to sterilize between uses. This increases the likelihood of transmitting infectious diseases or causing chemical damage to the cornea from residual antiseptic coming into contact with the patient's eye.

SUMMARY OF THE INVENTION

An applanation tonometer and method for measuring intraocular pressure are described herein. The invention allows for accurate measurement of intraocular pressure while addressing some of the deficiencies of existing tonometers.

In one embodiment, an applanation tonometer for flattening the cornea of an eye is provided, wherein the applanator comprises a fiberoptics array; a force transducer for measuring forces applied by the applanator; an image transducer for obtaining data regarding an image of the applanated eye; and a processing circuit configured to calculate an intraocular pressure of the eye from at least a measured force and corresponding measured geometrical property. In aspects of the preferred embodiment, the geometrical property of the image may comprise an area, diameter, or major and minor axes of the cornea of the applanated eye. The tonometer may further comprise a light source for illuminating the eye, and a lens system adapted to focus an image of the applanated portion of the eye from the applanator to the image sensor. Advantageously, an embodiment of the tonometer calculates an intraocular pressure using a plurality of corresponding forces and geometrical properties of the applanation image. In another aspect of a preferred embodiment, the tonometer is provided with a disposable tip that covers the applanator, thereby providing a replaceable, sterile interface between the tonometer's applanator and a patient's eye.

In another embodiment, a method of determining an intraocular pressure of an eye comprises applanating a portion of an eye of varying degree over time, acquiring data relating to the forces required to applanate the eye and the geometry of applanated portions of the eye, determining a slope of a line defined by these of data points, and calculating the intraocular pressure using this slope and a predetermined relationship. In a preferred embodiment, the data acquisition is synchronous.

In another preferred embodiment, a disposable tip for use with an applanation tonometer comprises a light-transmitting applanating region adapted to fit over an applanator of a tonometer, the applanating region having a surface adapted to optically couple with an applanator and another surface adapted to contact an eye, and an attachment mechanism for detachably attaching the tip to a tonometer. In an aspect of this preferred embodiment, the surface of the tip used to contact the eye has a matte finish, and the applanating surface of the tonometer's applanator has a matching flat, polished surface. Preferably, the tip is sterilized, and may further be packaged within a sterile environment. Advantageously, the tip may further incorporate a key fitting for attaching to the tonometer.

The tonometer embodiments described herein apply broadly and may take any one of various forms, such as a portable, hand-held device or a device uniquely designed to be used in conjunction with a slit-lamp.

DETAILED DESCRIPTION OF THE PREFERRED EMBODIMENTS

Applanation tonometers measure the intraocular pressure of an eye indirectly. In applanation tonometry, a portion of the cornea of a patient's eye is flattened (or applanated) by a probe. The force, or pressure, required to applanate a portion of the patient's cornea is measured, as is the applanated area of the eye. The intraocular pressure of the eye is calculated from those data. In some cases, several pairs of force and applanation data are used to calculate intraocular pressure.

Figure 1:
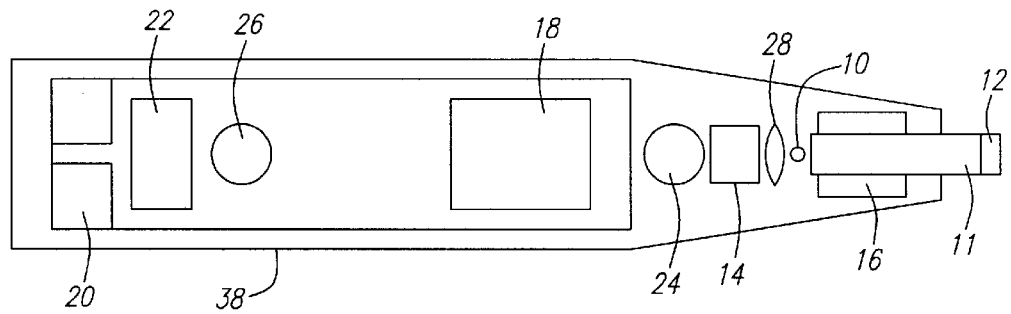
FIG. 1 is a general diagram of an applanation tonometer in accordance with an embodiment of the invention.

The schematic of an applanation tonometer according to a preferred embodiment is shown in FIG. 1. The tonometer shown and described herein is a portable, hand-held device; however, the teachings disclosed herein can be applied either to a portable, hand-held device or to a slit-lamp device, both of which are well known in the art. In the slit-lamp embodiment, the tonometer might be designed similar to existing Goldmann tonometer mounts. As depicted in FIG. 1, one embodiment of the hand-held device preferably comprises a light source 10; an applanator 11 for flattening a portion of the cornea; a disposable tip 12; an image sensor 14; a force sensor 16; a processor 18; a power supply 20; a display 22; manual controls 24, such as a user switch; an enunciator 26; and a lens system 28.

The applanator 11 is used as a flattening surface to flatten a portion of the cornea of a patient's eye. The distal end of the applanator 11 is flat, designed for applying pressure to the cornea to applanate it. The applanator 11 may be used in conjunction with a disposable tip 12 for sterilization purposes, as described below. The cross section of the applanator may be square, circular, or any other shape suitable for applanating a patient's cornea. In a preferred embodiment, however, the cross section of the applanator 11 is designed to be large enough and shaped so that it completely encompasses the largest applanated area of a cornea for which the tonometer is designed. For example, a 6 mm diameter applanator would be required to reliably flatten 5 mm of the cornea. In another preferred embodiment, the distal end of the applanator 11 comprises an optical-quality circular surface of less than 10 millimeters in diameter.

In addition to flattening a portion of a patient's eye, the applanator 11 serves to transmit an image of the applanated eye therethrough. In one innovative aspect of a preferred embodiment, the applanator 11 comprises a fiberoptics array. Using a fiberoptics array advantageously collimates images, conducts illumination and reduces reflection. The array preferably comprises a bundle of fibers, but the bundle is fused together thereby making it appear as a solid rod. This rod can be machined as if it were a solid glass rod. Fiberoptics arrays suitable for this application are commercially available, such as those made by Collimated Holes, Inc. of Campbell, Calif.

When an applanator 11 comprising a fiberoptics array is pressed against a patient's eye at a distal end, the applanator 11 reproduces an image of the applanated eye at the opposite, proximal end thereof. As described in further detail below, the image sensor 14 is adapted to receive this image of the applanated eye from the proximal end of the applanator 11 and to generate data relating to the applanated eye—such as area or diameter—using that image.

Where the applanator 11 comprises a fiberoptics array, the diameter of the fibers of the fiberoptics array determine the resolution of an image that is transmitted from the proximal end of the fiberoptics array to the distal end. Therefore, the fiber density of the fiberoptics array is related to the resolution of the image of the applanated cornea on the proximal end of the applanator 11. The resolution of this image determines the precision for which applanation data (e.g., area and diameter of the applanated portion of the eye) can be obtained by the image sensor 14. Accordingly, the fiber density of the fiberoptics array is preferably selected to be fine enough to allow images having a resolution suitable for deriving therefrom useful data. In an exemplary embodiment, the fiber density of the fiberoptics array can be selected to be finer than approximately the pixel size of the sensor. An example image sensor is a Kodak KAC-0311 640×480 pixel VGA CMOS Image Sensor. An example pixel size therefor is 7.8 micrometers×7.8 micrometers.

Figure 2A:
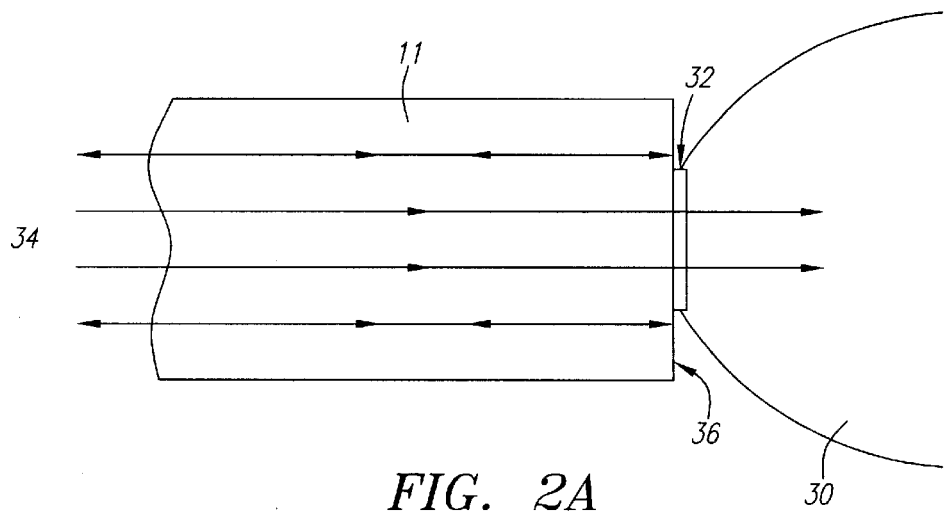
FIG. 2A is a schematic drawing of an applanator flattening a portion of a patient's eye in accordance with a preferred embodiment.

FIG. 2A shows a schematic drawing of an applanator 11 flattening a portion of a patient's eye 30 in accordance with a preferred embodiment. At portions of the eye 30 where the applanator 11 flattens the eye 30, a tear film 32 develops. Light rays 34 are shown diagrammatically in FIG. 2A as arrows, their arrow heads showing the direction that the light rays 34 propagate. In some cases, as shown by the arrows, the light rays 34 propagate in both directions along a single path. In addition, it can be seen that the light rays 34 are collimated, which yields a precise and accurate image of the applanated portion of the patient's eye 30. Collimated light is one benefit of using a fiberoptics array for an applanator 11, as described in detail above.

It is well known in the art that when light travels through a first medium and meets the boundary between the first medium and a second medium, the light may cross the boundary into the second medium or it may be reflected. The amount of light reflected depends on the relative indices of refraction of the two media. Where the index of refraction of the first medium is significantly higher than that of the second (e.g., as where the index of refraction of the applanator 11 is much higher than the index of refraction of the air), the light will substantially reflect back into the first medium. Where the index of refraction of the first medium is not larger than that of the second (e.g., as where the index of refraction of the applanator 11 is about the same or less than that of the tear film 32 and eye 30), the light will substantially continue into the second medium. The result of this phenomenon is shown in FIG. 2A. If a light ray 34 travels within the applanator 11 and hits the distal end 36 at a point where the applanator 11 contacts the eye 30, the light 34 continues through the tear film 32 and exits the applanator 11. In contrast, if light 34 traveling within the applanator 11 hits the distal end 36 at a point where the applanator does not contact the eye 30, the light 34 reflects back.

Figure 2B:
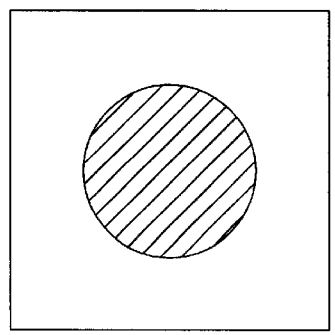
FIG. 2B is a cross section diagram of an exemplary image of an exemplary applanated eye in accordance with a preferred embodiment.

FIG. 2B shows a cross section diagram of an exemplary image of an applanated eye that would be seen from a proximal end of the applanator 11, in accordance with a preferred embodiment. In the image, applanated portions of the eye appear as dark areas while the other areas appear light. This follows because the light traveling through the applanator 11 reflects back only at points on the distal end 36 where the applanator 11 does not applanate the eye 30. Because, in a preferred embodiment, the applanator 11 comprises a flat surface used to flatten a substantially spherical eye 30, the image of the applanated portion of the eye generally comprises a circle or oval, as depicted in FIG. 2B.

The tonometer may rely on ambient light or, advantageously, may further comprise a light source 10 configured to illuminate the applanator 11, as shown in FIG. 1. The light source 10 may comprise any of a wide variety of light sources known in the art, including visible and invisible light emitting diodes, incandescent and fluorescent sources, configured as point or linear sources or configured as illumination rings. Diodes are particularly advantageous for portable hand-held embodiments due to their conversion efficiency, illumination stability, long life and mechanical durability.

The light source 10 may emit white light, or it may be filtered to emit only certain specific wavelengths. In the latter case, by operating in a narrow light spectrum, the image of the applanated cornea can be filtered to that wavelength prior to being read by the image sensor 14. This filtration is accomplished, for example, by a light filter between the applanator 11 and the image sensor 14. Moreover, the light filter can be integrated as part of the lens system 28 for increasing the contrast of certain features as well as accommodating the use of visible and fluorescent dyes.

In another innovative aspect of the preferred embodiments, a disposable tip 12 is installed over the distal end of the applanator 11. The disposable tip comprises a translucent or transparent membrane. In a preferred embodiment, the disposable tip 12 comprises polyethylene fibers fused into a sheet. The disposable tip 12 is adapted to cover at least the portion of the applanator 11 that applanates a patient's eye. Use of sterile disposable tips 12 in connection with the tonometer, preferably changing the tip 12 between patients, eliminates the need to sterilize the applanator 11 between patients. Sterilizing the applanator 11 often involves use of chemical cleaning agents, which may irritate or damage a patient's cornea. Sterile disposable tips 12, however, may be individually packaged and installed before use without chemicals. In addition to promoting sterility, the disposable tip 12 serves to diffuse reflected light and enhance the optical contrast between the contacted and non-contacted surfaces of the tip.

A variety of techniques for attaching the tip 12 to the tonometer can be utilized, and many can be envisioned by those skilled in the art. In accordance with one advantageous aspect of the invention, the disposable tip 12 is preferably designed to uniquely attach to the tonometer.

The tip 12 of the tonometer is an important part of the system for two reasons. First, it provides a barrier between the eye of the patient and the distal end of the applanator 11, and is a disposable tip, so as to prevent cross contamination from patient to patient. Second, it provides desirable optical properties (namely a matte surface that faces the eye) to best couple the light rays with the tear film 32. An example disposable tip 12 can comprise a single sheet of plastic material which will be discussed in more detail later and which is securely retained over the end of the tip of the tonometer by a removable elastic ring. Controlling installation of the disposable tip 12 in this way, thereby keeping membranes not designed for use with this tonometer design from being used, helps to maintain instrument system performance and thus increases patient safety.

Preferably, the disposable tip 12 is optically coupled to the applanator 11, having a substantially equivalent index of refraction. In the present system, it has been found that a polished applanating surface—e.g., the surface that actually contacts the patient's eye to thereby flatten it—can lead to spurious and low contrast reflections and thus poor image quality. Using a matte surface for applanating the cornea, it has been further discovered, reduces these problems. Where a disposable tip 12 is used, the applanating surface is the surface of the tip 12. Where no disposable tip 12 is used, the tonometer's applanating surface is the distal end of the applanator 11. Therefore, in a preferred embodiment, a disposable tip 12 has a matte surface on its outer surface, which contacts the patient's eye during use, to reduce these undesired optical effects. In addition, the tip 12 is smooth on its inner surface, which contacts the applanator 11. The smooth surfaces of the applanator 11 and tip 12 promote efficient transfer of light between them. It can thus be appreciated that this leads to an added benefit that this feature helps to enforce use of the disposable tip 12. By providing a matte outer surface of the disposable tip 12 and polishing the distal end of the applanator 11, the tonometer will operate accurately with a tip 12 installed, and may operate poorly or not at all without a tip 12 installed. This, in turn, helps to require the user of the tonometer to use the sterile disposable tips 12 with the tonometer, thus promoting patient safety. Preferably the outer surface of the applanator 11 and inner contact surface of the tip 12 are both flat.

When the tonometer is used to applanate a portion of a patient's eye, an image of the applanated surface of the eye is transmitted through the tip 12 and applanator 11 onto the proximal end of the applanator 11, as described in detail above. The image sensor 14 is adapted to read an image formed at the proximal end of the applanator 11. In one embodiment, the image sensor 14 comprises a monochrome or color charge-coupled device (CCD) or complementary metal oxide semiconductor (CMOS) device that comprises a two-dimensional array of cells (pixels) for imaging the applanated corneal surface.

The image sensor 14 further comprises circuitry that analyzes the image of the applanated portion of the cornea. From that image, the circuitry generates a signal that relates to a geometric property of the applanated portion of the eye. This geometric property may be an area or a diameter of the circular image, or major and minor axes of an elliptical image, any of which can be used in conjunction with force data to calculate intraocular pressure. Given the image data produced by the image sensor 14, it can be appreciated that a variety of techniques and algorithms can be employed to determine the area, diameter, or axes of the applanated portion of the patient's eye. For example, a storage intensive method could be employed, which would require more memory but less processing power. Alternatively, an interframe or intraframe processing methods could be employed, which would require less memory but more processing power in embodiments involving high frame capture rates. For example, where a video capture rate is 30 frames per second, there would be approximately 33 milliseconds between frames. In addition, the tonometer employs discrimination algorithms to determine whether the image is sufficiently centered and to determine the location of the edge of the image of the applanated cornea.

Further, the determination of the required applanation parameter (e.g., applanation diameter) may be performed by circuitry accompanying the image sensor 14 or by the processor 18. In the latter case, the image data would be sent from the image sensor 14 to the processor 18.

In another aspect of a preferred embodiment, the image formed at the proximal end of the applanator 11 is passed through a lens system 28, which may comprise one or more lenses and mirrors. The lens system 28 is adapted to focus an image of the applanated portion of the eye from the proximal end of the applanator 11 and onto the image sensor 14.

A force sensor 16 is operatively coupled to the applanator 11 for measuring forces applied to the eye by the applanator 11. In a preferred embodiment, the force sensor 16 comprises a piezoelectric element in a "washer" or "doughnut" shape. Such a configuration provides a clear optical path through the center axis. A piezoelectric element has a further advantage of requiring extremely small displacements for a given applied force. The use of an axially polarized piezoelectric element provides for a high relative voltage (corresponding to a high force signal) per actual force applied thus resulting in low cost, and low variability of electrical characteristics that simplify the manufacturing process. When a piezoelectric device is used, the piezoelectric element is preferably selected to have a large enough diameter, given the forces involved, so that the piezoelectric element will not operate within its nonlinear range. In addition, the force sensor 16 is preferably loaded into the tonometer housing 38 free from static forces other than the applanator 11.

In a preferred embodiment, the force sensor 16 is used in conjunction with circuitry filters out high-frequency noise in the force signal. For example, multiple-pole band pass filter might be appropriate, depending on the design parameters of the tonometer. Further, the force sensor 16 may include AC coupling circuitry for eliminating undesirable base-line drift.

A processor 18 is communicatively coupled to the image sensor 14 and force sensor 16. The processor 18 may comprise analog or digital circuitry, and preferably comprises a microprocessor and associated electronics. In a preferred embodiment, the processor incorporates multi-layered, flat-mount circuit board and/or hybrid microcircuit or chip-onboard technology. As described below, the processor 18 is adapted to calculate an intraocular pressure of the eye using force and applanation data from the image and force sensors 14,16. In addition, the processor 18 is preferably coupled to the other elements of the tonometer, wherein the processor 18 controls the functionality of the tonometer as described herein.

In a preferred embodiment, the tonometer further includes a display 22 for displaying the calculated intraocular pressure to the user. The display may incorporate technology such as LCD, LED, or any other technology known in the art. The display 22 is communicatively coupled to the processor 18 for receiving the calculated intraocular pressure and other data and/or commands. In addition, the tonometer may further include an enunciator 26 for the transmission of audible signals. The enunciator 26 is coupled to the processor 18, wherein the processor 18 causes the enunciator 26 to play one or more sounds upon certain conditions, such as "ready to begin" and "test completed" sounds. Advantageously, the enunciator 26 may be designed to play a unique sound upon certain events, like when the system determines that a correct intraocular pressure has been obtained. Manual controls 24, such as a power switch, may also be provided. The enunciator may also be used to optimize the user's rate of applanation-de-applanation by varying the frequency or amplitude of the sound.

The electronics of the tonometer are preferably powered by one or more low voltage, easily replaceable batteries 20, which are preferably located in a rear or bottom compartment for hand-held embodiments or in a lower compartment for slit-lamp embodiments. Preferably, standard disposable or rechargeable camera or watch-type batteries are used in conjunction with diode protection in hand-held embodiments. In slit-lamp mounted embodiments, an external transformer is preferably used with AC/DC power conversion, as needed.

According to a preferred embodiment, force and applanation data are acquired simultaneously by the force and image sensors 16 and 14, respectively. In one aspect of the preferred embodiment, the data are acquired at a rate of 30 Hz, but the typical range can be 20 Hz to 60 Hz to obtain as many measurements as possible. Using synchronous data acquisition, each force datum corresponds time wise to an applanation datum. These pairs of data are stored and used by the processor to calculate the intraocular pressure of the eye, as described below. Advantageously, the processor 18 may be operatively coupled to the image and force sensors 14 and 16, wherein the processor 18 controls and coordinates their operation. By automating the data acquisition, the processor 18 can increase reliability and accuracy of the system. In addition, the force sensor 16 can be used to activate the image sensor 14 to begin the data acquisition process. This could be achieved, for example, by adapting the processor 18 to periodically receive signals from the force sensor 16. Upon an initial force signal from the force sensor 16, which would signify that the applanator 11 is in contact with the eye, the processor would begin the data acquisition process.

Figure 3:
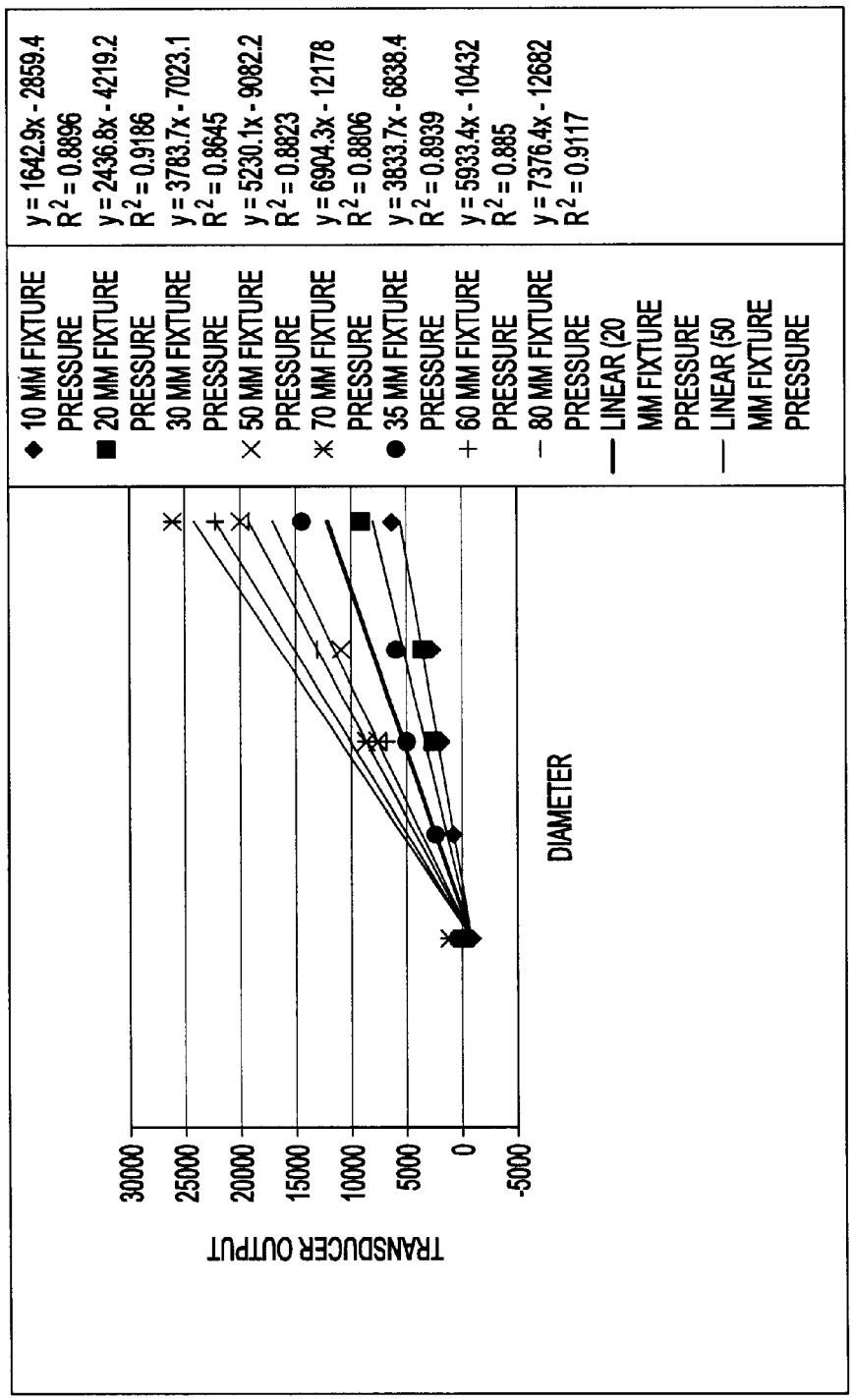
FIG. 3 is a graph of sample data of applanated diameter plotted versus force sensor output for various values of simulated intraocular pressure.
Figure 4:
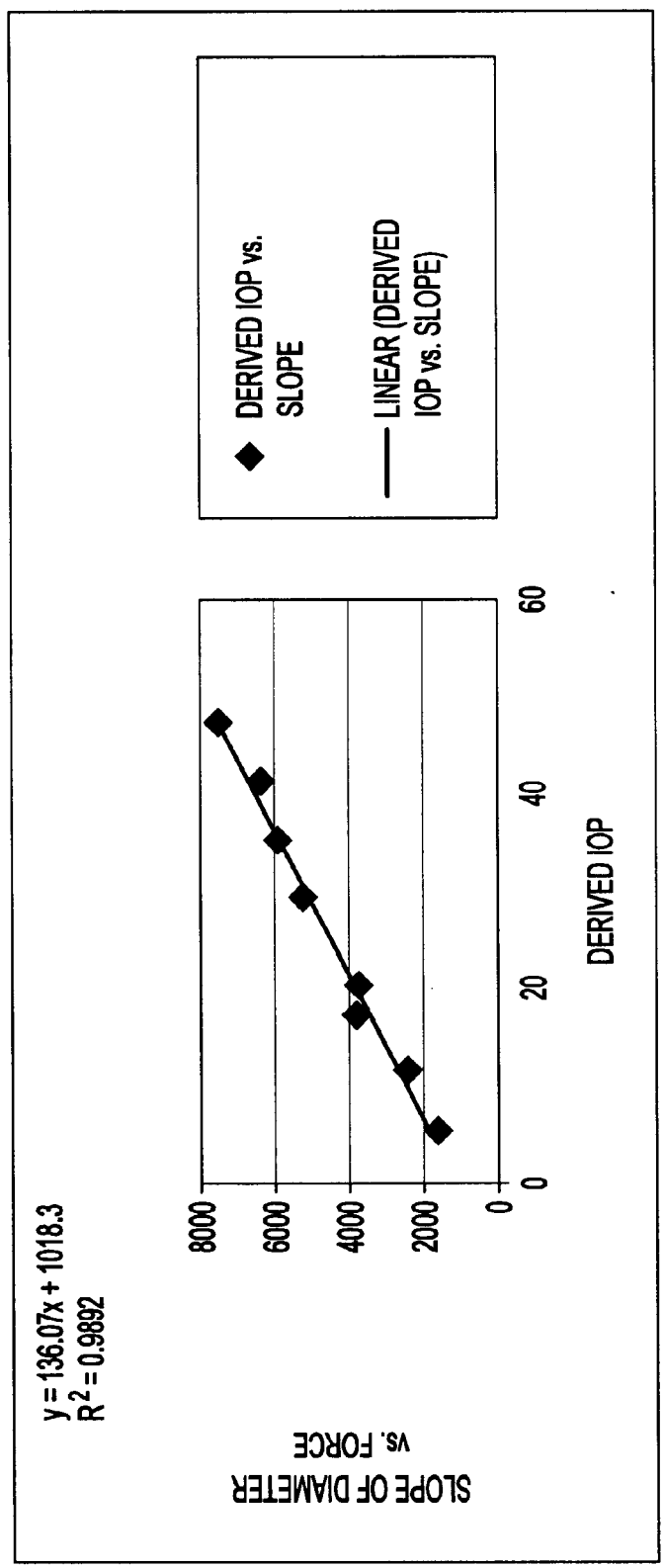
FIG. 4 is a graph of derived intraocular pressure versus slope of the plots of FIG. 3.

Using data generated by a tonometer in accordance with a preferred embodiment, FIG. 3 shows graphs of applanated diameter versus force transducer output (which is proportional to the force applied) for simulated eyes having various values of simulated intraocular pressure. As FIG. 4 shows, it has been discovered that the slopes of the lines plotted in FIG. 3 (defined by the force and applanated diameter locus of data points) can be plotted relative to the intraocular pressure corresponding to each line. This reveals a linear relationship between this slope and intraocular pressure. Accordingly, the intraocular pressure can easily be determined from that slope, which in turn can be determined from a set of data points of force versus applanated diameter for an eye.

To take advantage of this, the processor 18 of the tonometer maintains a plurality of measurements from the force and image sensors 16 and 14, as explained above. In one embodiment, the readings of the pressure sensor 16 and image sensor 14 are synchronized by the processor 18 at around 30 frames per second. The processor 18 then calculates the slope of the line defined by the relationship between the force sensor 16 and applanated diameter, and, according to the predetermined linear relationship, the processor 18 calculates the intraocular pressure of the eye. Preferably, the enunciator 26 signals that the test is complete, and the calculated intraocular pressure is displayed on display 22.

Figure 5:
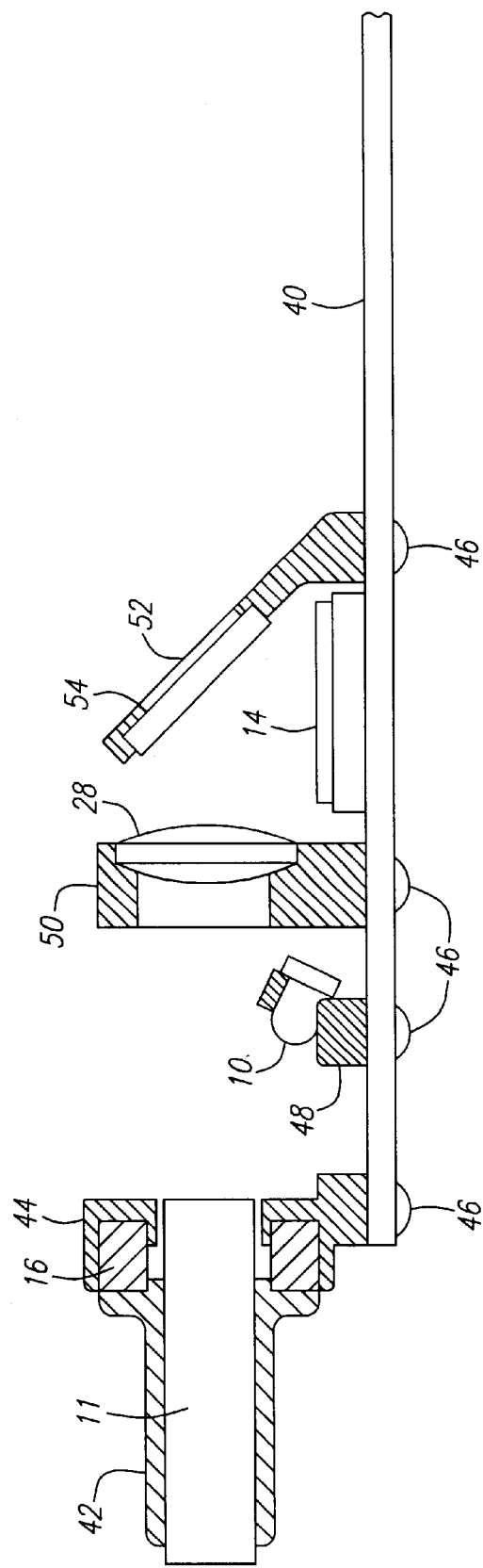
FIG. 5 is an exemplary optical element layout of an applanation tonometer.

FIG. 5 illustrates in detail the entire optical layout of an embodiment of the present invention. The various components are mounted on a component board 40. As shown, a mounting tube 42 which holds the fiber optic array of the applanator 11 is coupled with the force transducer 16 and mounted in a mounting bracket 44 attached by a screw or other fastener 46 to the board 40. In this embodiment, an LED 10 functions as the light source and is mounted on the board 40 via a bracket 48. The lens 28 is mounted and supported in a bracket 50. The image sensor 14 is disposed on the board 40. A folding mirror 52 is mounted to the board 40 via a bracket 54 and serves to direct the image to the image sensor 14. Other components, such as the processor, power supply, and the like are suitably mounted to the component board 40 but are not shown in FIG. 5.

Discussed below are several modes of operation and additional information concerning components and controls.

1. Calibration
    a. External—compressible test block that is used to generate:
        i. Standardized diameter-force curve when applied to the instrument;
            1. Artificial corneal membrane,
            2. With simulated intraocular pressure source.
        ii. Standardized optical test pattern.
    b. Internal—Adjust the image quality for optimum image for analysis.
        i. Illumination intensity—Rheostat adjustment or digital to analog adjustment under program control.
        ii. Imaging sensor gain—Sensor parameter settable by programming, static or dynamic during image capture.
        iii. Or both.
    c. Non volatile storage—A means of storing the results of calibration in an electronic memory such as EEPROM that is durable between power cycles but can be overwritten by the microprocessor with new calibration factors over the expected life of the instrument.
    d. Force transducer check—confirm that the weight of the fiberoptic array as measured by the force transducer, ascertained by changing the attitude of the instrument from pointing down to pointing up, is stored as a constant, provided it falls within known limits.
2. Corneal properties modes—
    a. Normal cornea (defaulted). Used for subjects known to have normal corneas.
    b. Thin cornea. Used for subjects know to have thin corneas, e.g., post Lasik.
    c. Thick cornea. Used for subject known to have corneal edema, or for veterinary use.
    d. Irregular cornea. For use in subjects known to have pathological states such as astigmatism.
3. Data storage and analysis mode.
    a. Store data for multiple subjects.
    b. Store unprocessed data for external processing.
    c. Perform statistics for multiple subjects or measurements.
4. Data communication mode.
    a. Wireless link to external devices:
        i. PDA
        ii. Desktop-laptop
        iii. Network
        iv. Proprietary microprocessor based product.

Image Processing Methods
1. Extraction of diameter. Determine diameter from the raw image. This method may be preferable in cases where the cornea is regular.
2. Total area. Determine total area by pixel count or other means. This method may be preferable where the cornea produces a non-circular image.
3. Major and minor axis. Determine the major and minor axis to correct for astigmatism.
4. Area of interest. Determine the area of interest based upon the centroid made by initial contact of the transducer tip with the cornea.
5. Specific auditory feedback including transient or continuous tones during the course of contact including, but not limited to:
    a. Off axis;
    b. Non-perpendicular
    c. Insufficient dwell time;
    d. Saturation;
    e. Incomplete contact;
    f. Good reading;
    g. Bad reading;
    h. Time out.

Figure 6A:
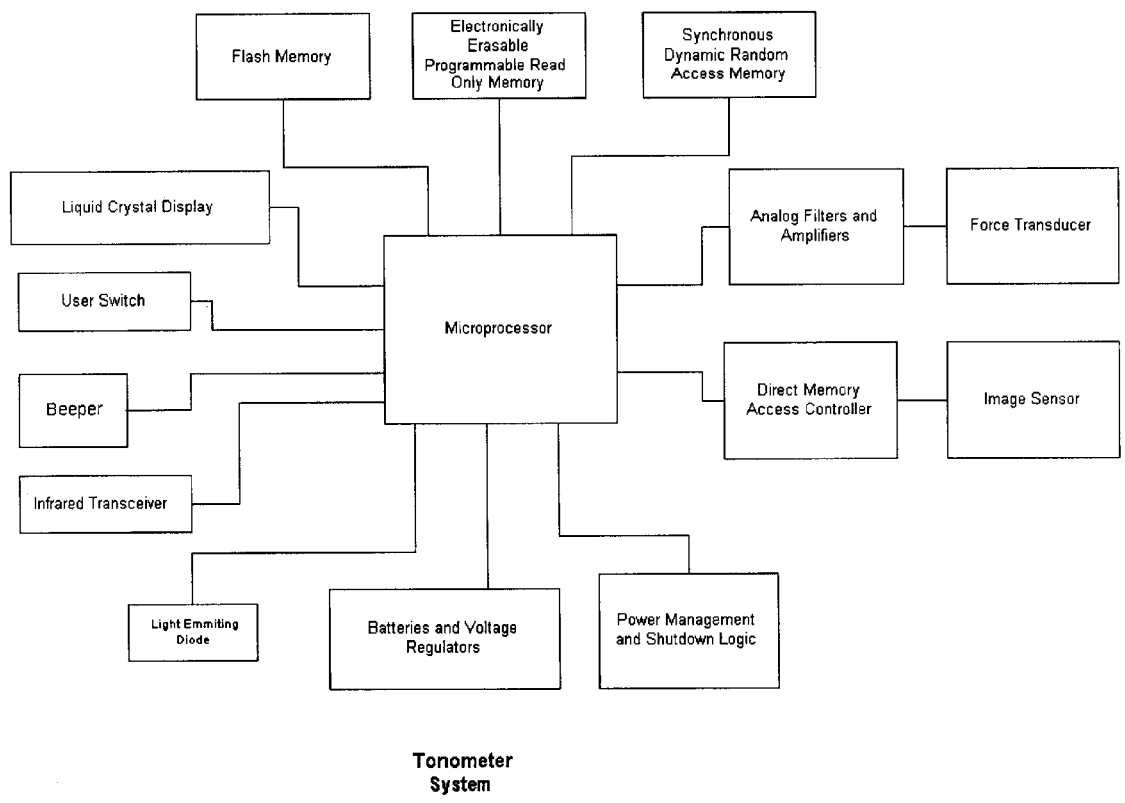
FIGS. 6a and 6b provide a block diagram of the overall tonometer system and the micro-processor subsystem respectively.
Figure 6B:
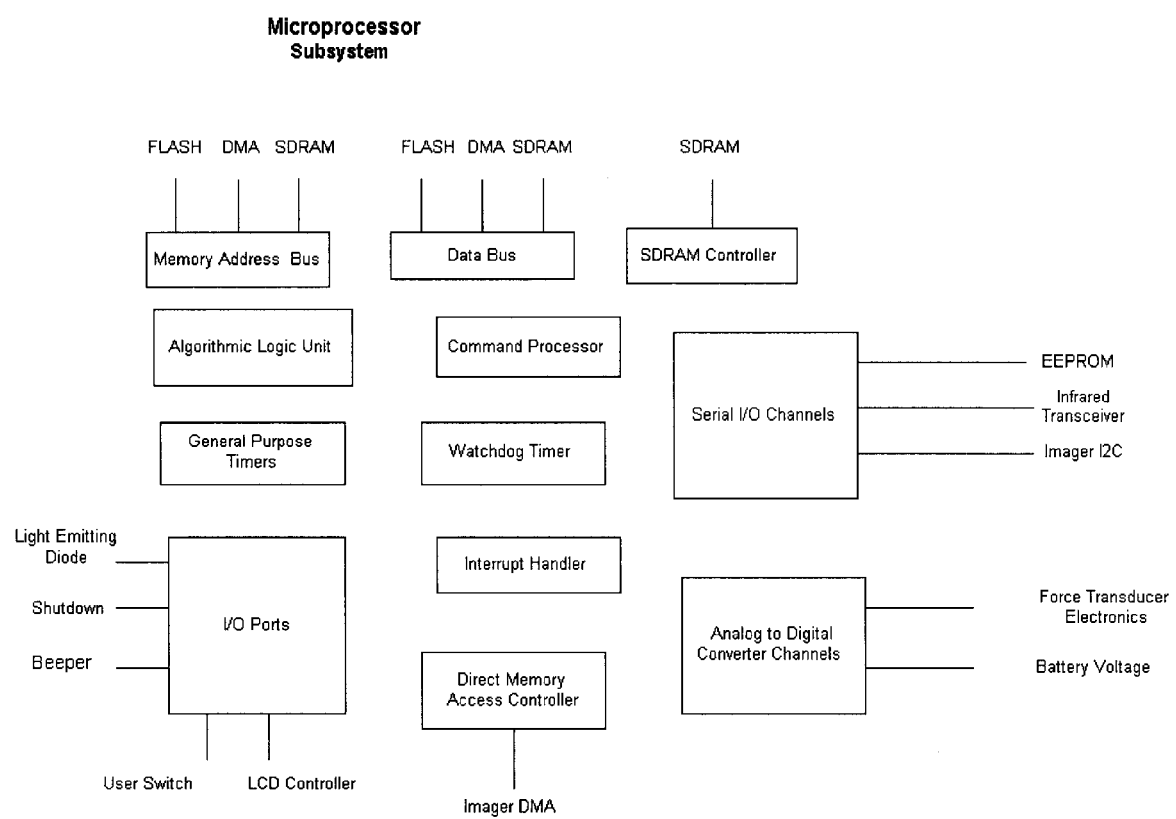

For the sake of completeness, FIGS. 6*a* and 6*b* are included wherein FIG. 6*a* illustrates the overall tonometer system which is controlled by the microprocessor 18. FIG. 6*b* illustrates an exemplary layout for the microprocessor, and it is believed that an understanding of FIGS. 6*a* and 6*b* is readily apparent to those skilled in the art.

FIGS. 7 through 17 are exemplary flow charts illustrating various operational aspects of a tonometer according to the present invention and as previously described. These illustrate the various steps in the acquisition of a reading, calculation of a result, as well as calibration techniques, and are readily understandable to those skilled in the art and are briefly described below.

Figure 7:
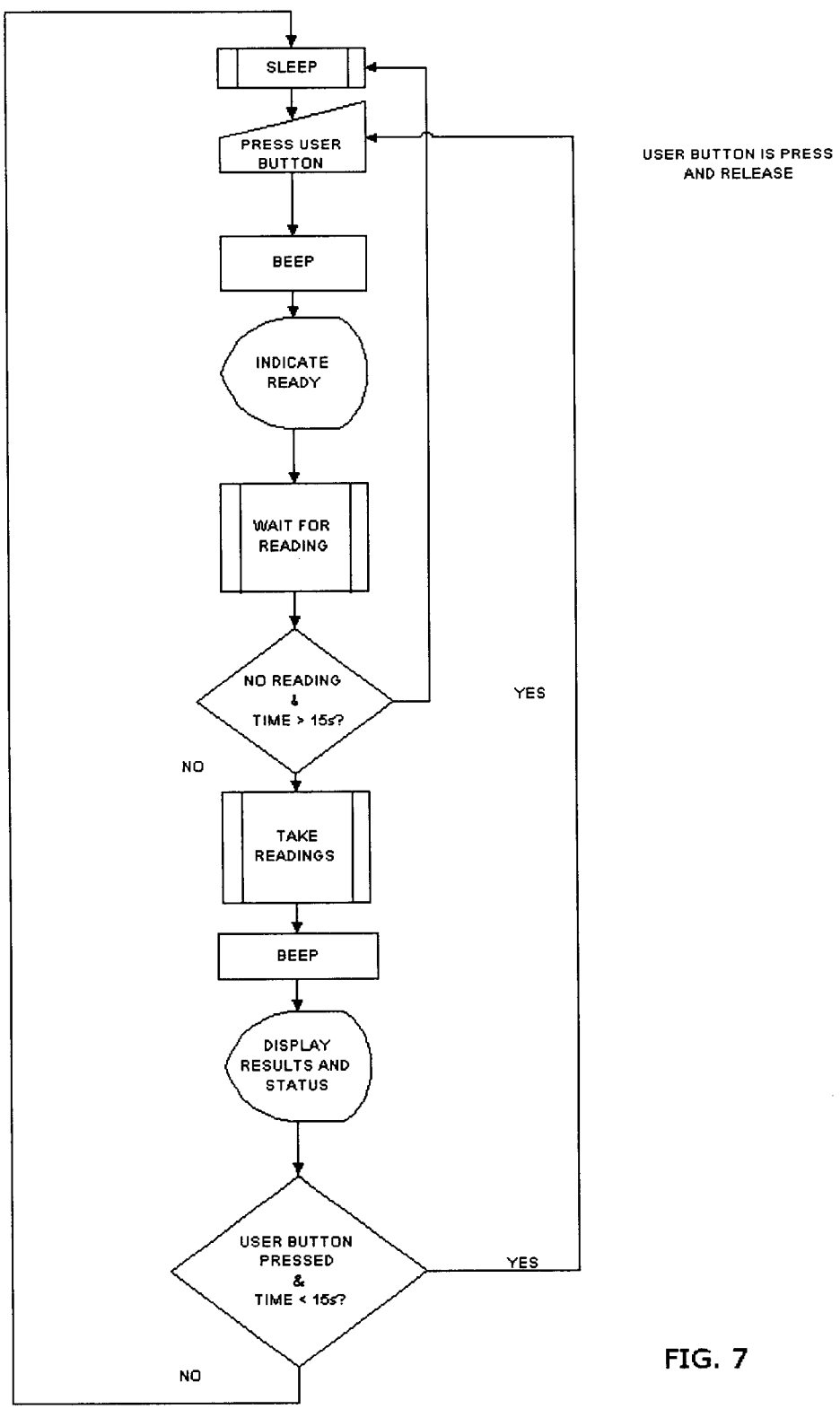
FIGS. 7 through 17 are flow charts indicating various operational aspects of an embodiment of the present invention.

The main tonometer loop is shown in FIG. 7. This flow loop is the main loop of operation for the tonometer system. The entry to the loop is out of "Sleep." A button press exits "Sleep." "Sleep" is reentered if the instrument is inactive for the prescribed period of time.

Figure 8:
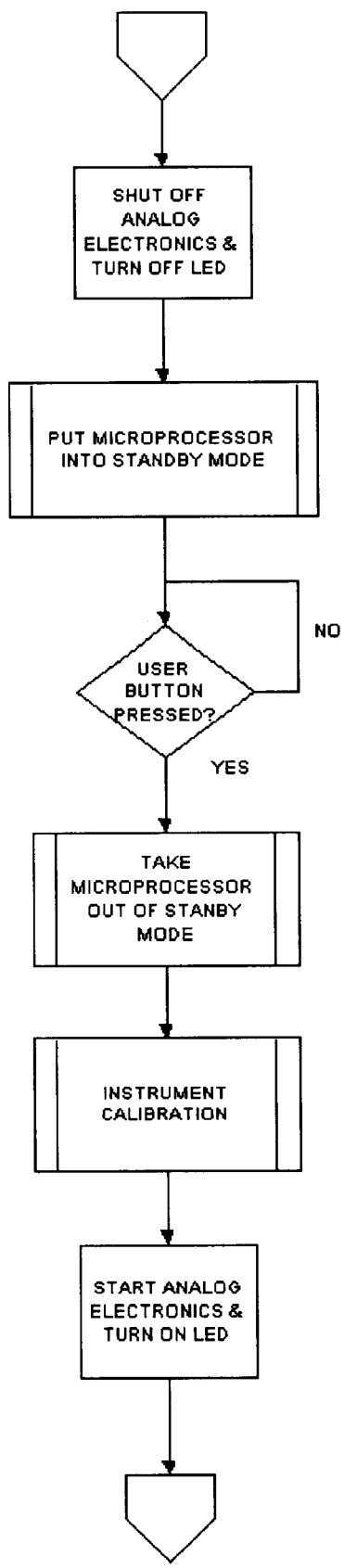

The "Sleep" process is shown in FIG. 8. This diagram is an expansion of the "Sleep" process block shown in FIG. 7. When the process is entered the systems are shut down and the instrument waits in the "User button Pressed" loop. If the user button is pressed, the loop is excited and the subsequent processes return the instrument to operational status.

Figure 9A:
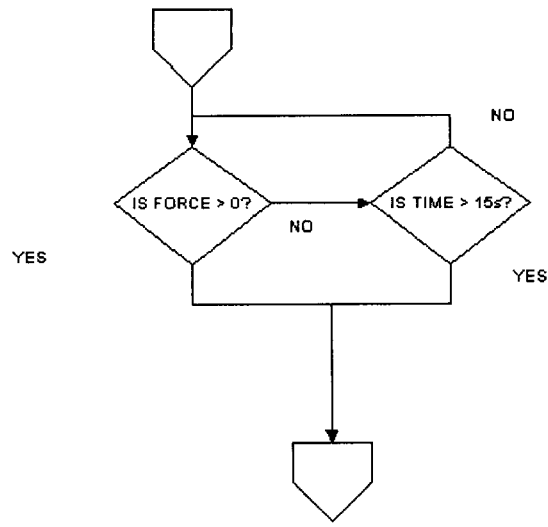

The "Waiting for Reading" process is shown in FIG. 9A. This diagram is an expansion of the "Waiting for Reading" process block shown in FIG. 7. The instrument either responds to an applied force or times out in this process.

Figure 9B:
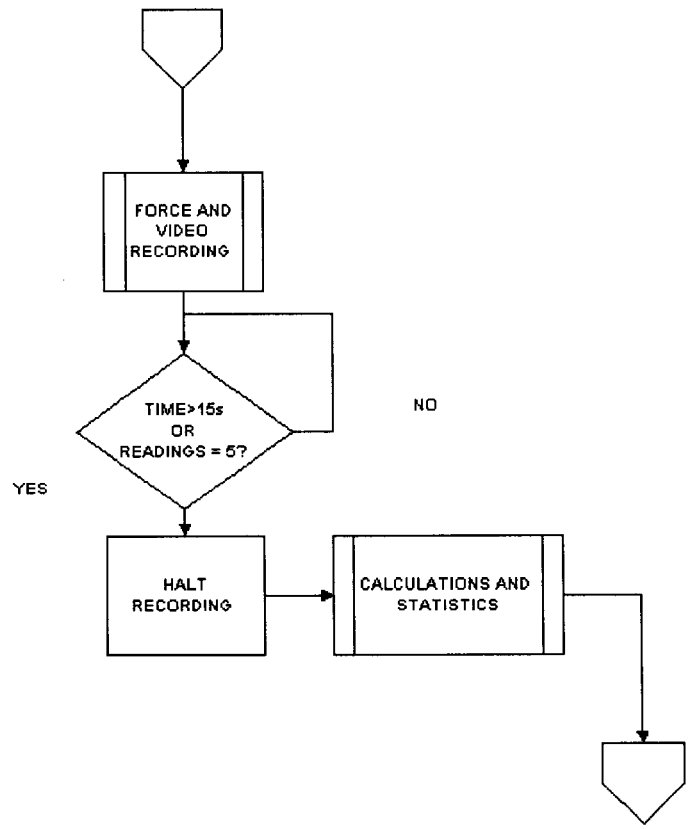

The "Take Readings" process is shown in FIG. 9B. This diagram is an expansion of the "Take Readings" process block shown in FIG. 7. This instrument records the patient information and performs the calculations and statistics in this process.

Figure 10:
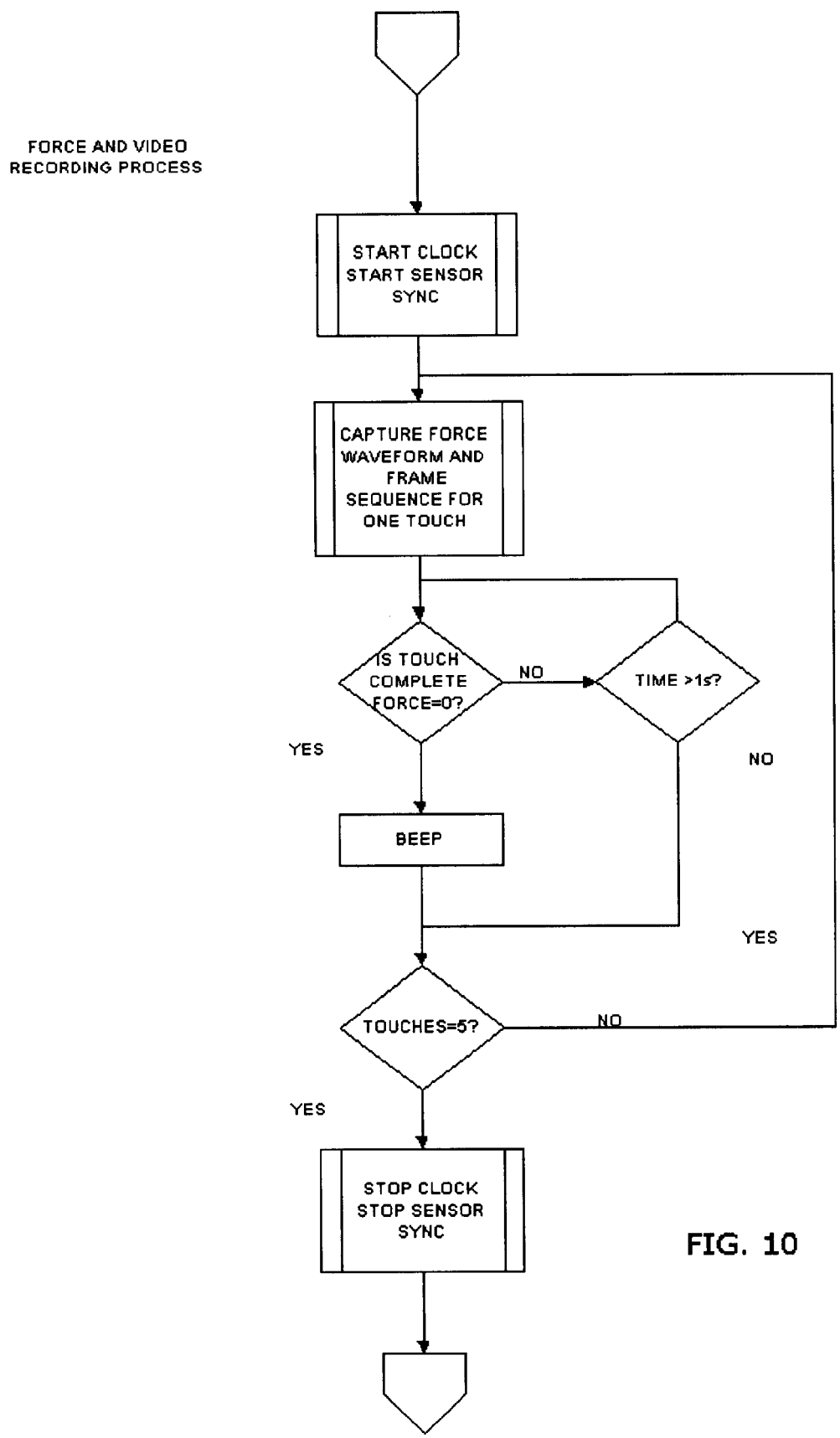

The "Force and Video Recording" process is shown in FIG. 10. This diagram is an expansion of the "Force and Video Recording" block shown in FIG. 9B. This process captures the data that will be used for the calculations.

Figure 11:
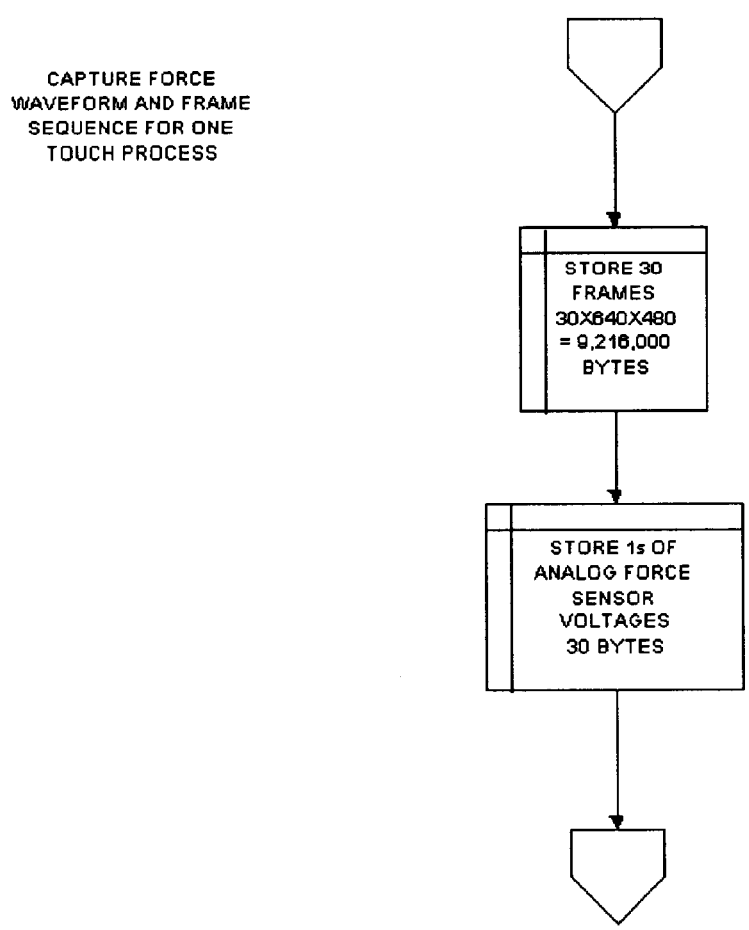

The "Capture Force Waveform and Frame Sequence for One Touch" process is shown in FIG. 11. This diagram is an expansion of the "Capture force Waveform and Frame Sequence for One Touch" block shown in FIG. 10. This process captures the data for one video frame and the associated force value that will be used for the calculations.

Figure 12:
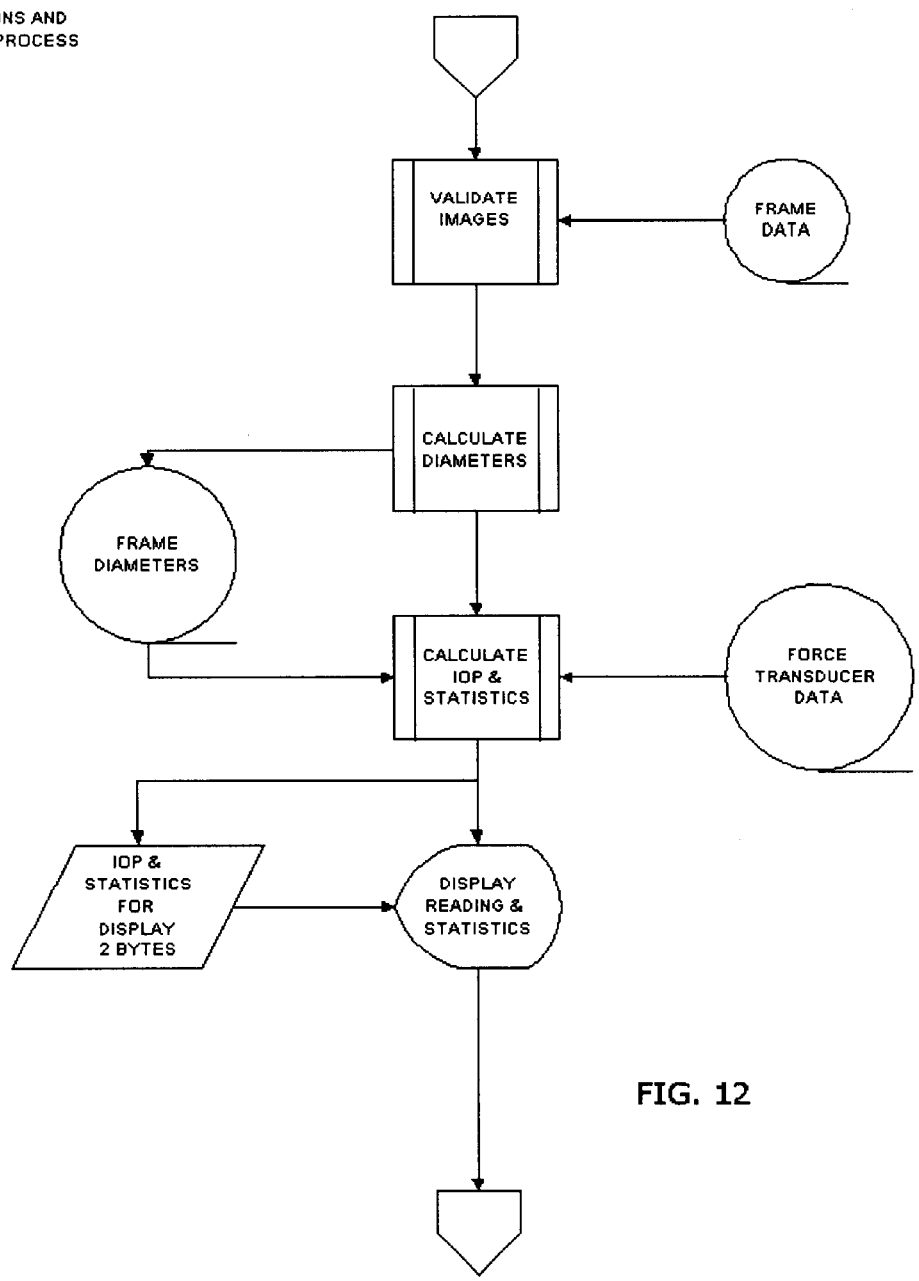

The "Calculations and Statistics" process is shown in FIG. 12. This diagram is an expansion of the "Calculations and Statistics" block shown in FIG. 9B. This process validates the data and performs the statistics processing.

Figure 13:
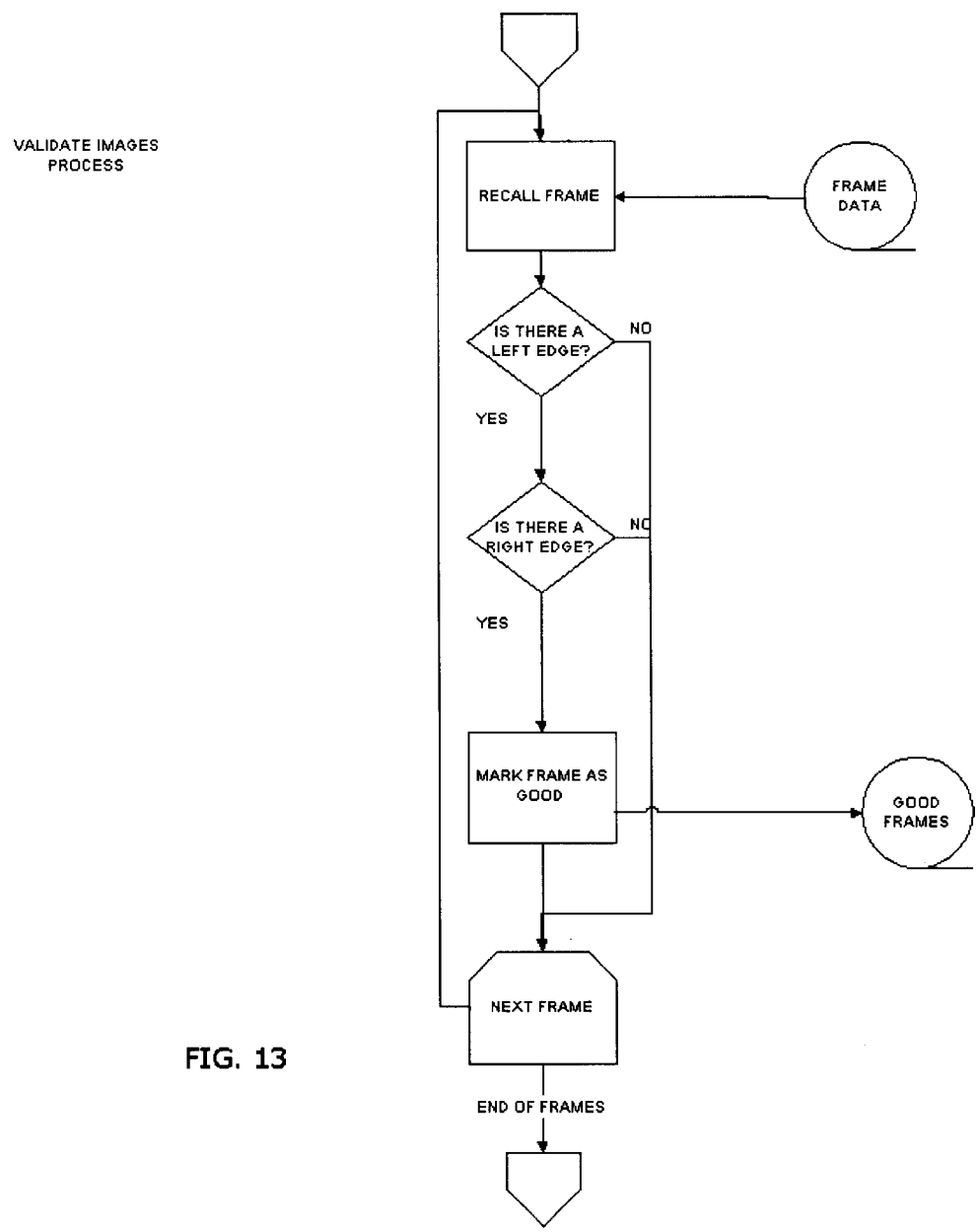

The "Validate Images" process is shown in FIG. 13. This diagram is an expansion of the "Validate Images" block shown in FIG. 12. This process validates the image data and rejects those that fail a certain criteria.

Figure 14:
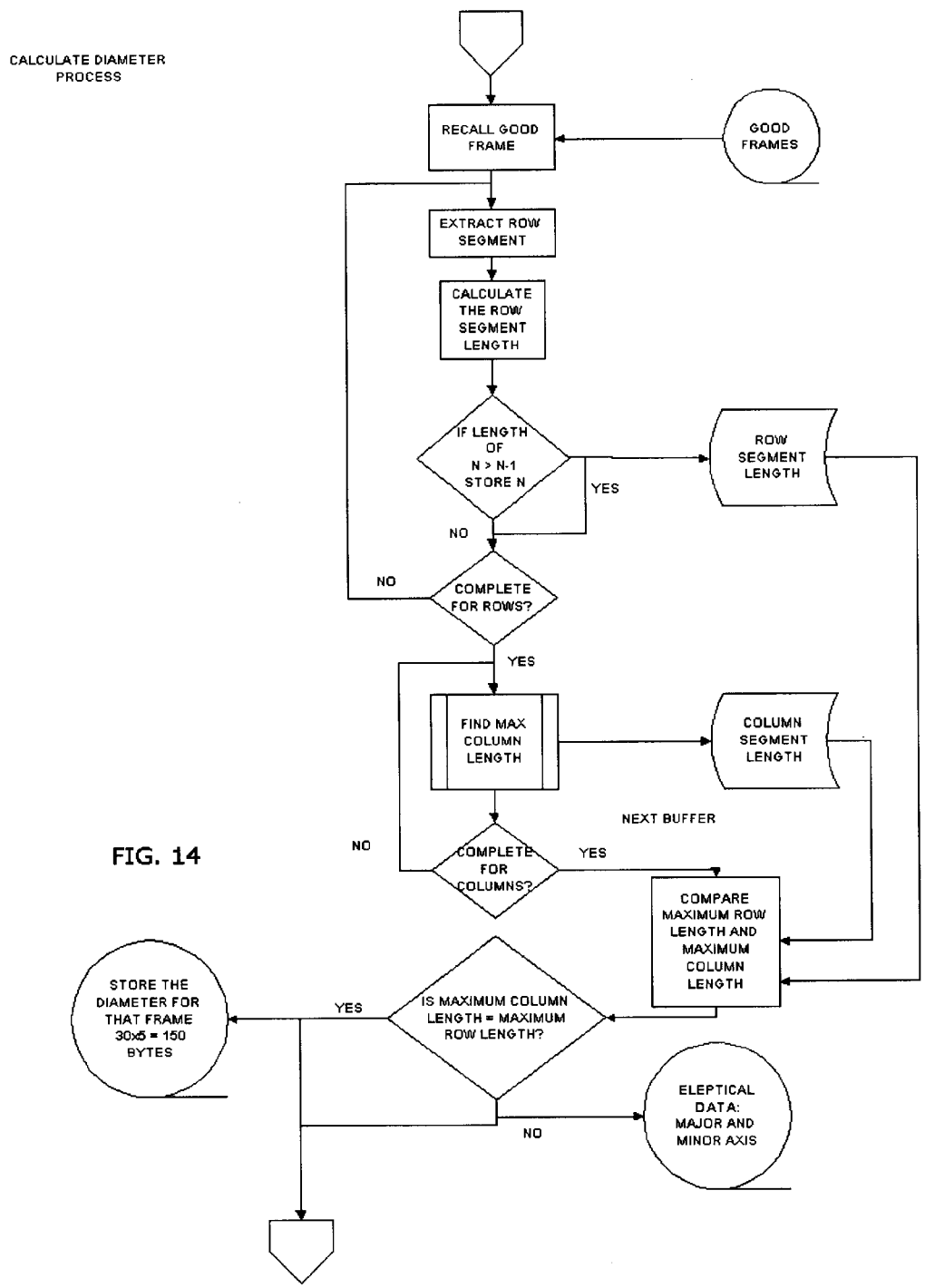

The "Calculate Diameter" process is shown in FIG. 14. This diagram is an expansion of the "Calculate Diameter" block shown in FIG. 12. This process determines the diameter of the image from the video data.

Figure 15:
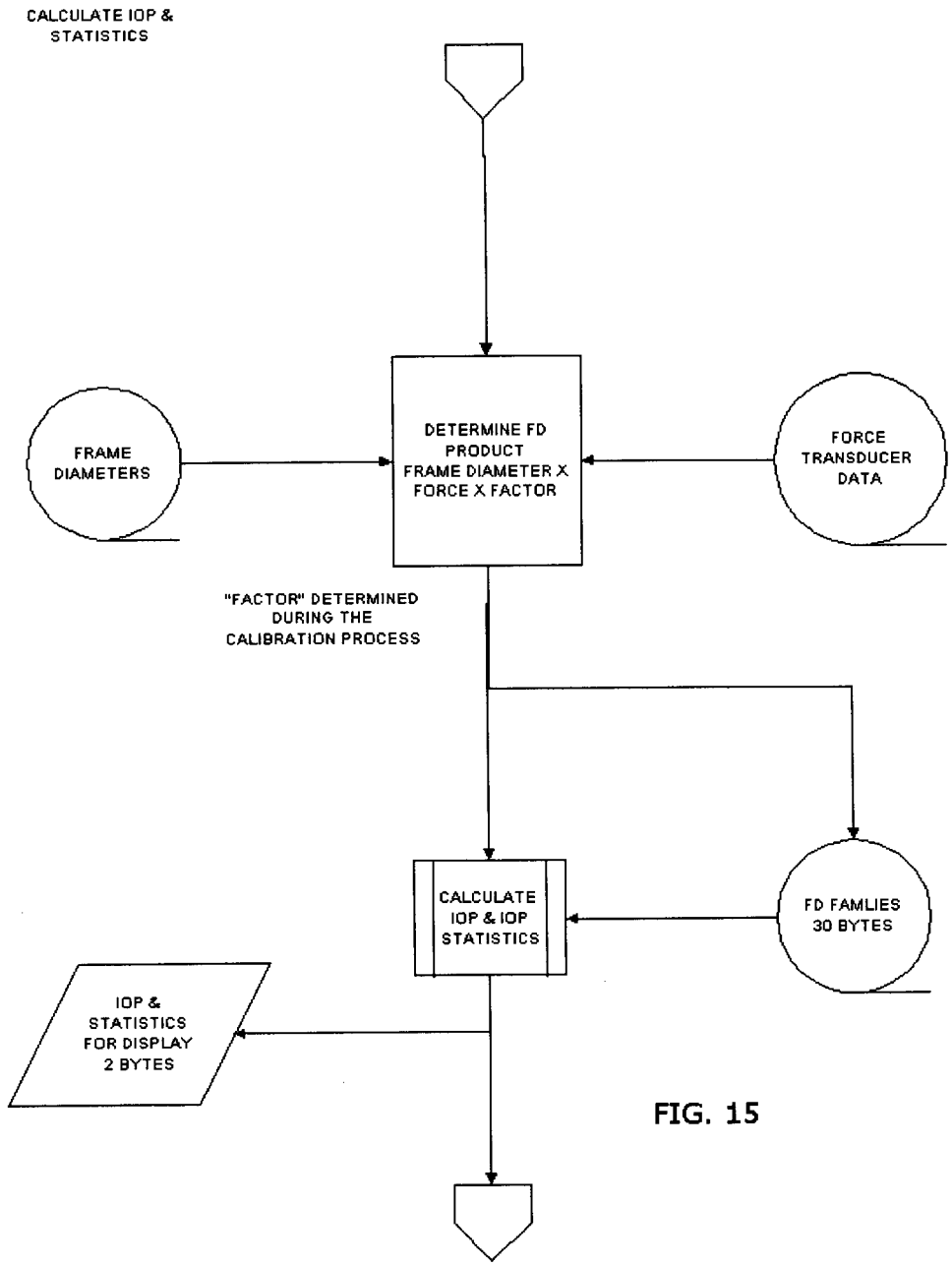

The "Calculate IOP and Statistics" process is shown in FIG. 15. This diagram is an expansion of the "Calculate IOP and Statistics" block shown in FIG. 12. This process determines the statistical fit of the data.

Figure 16:
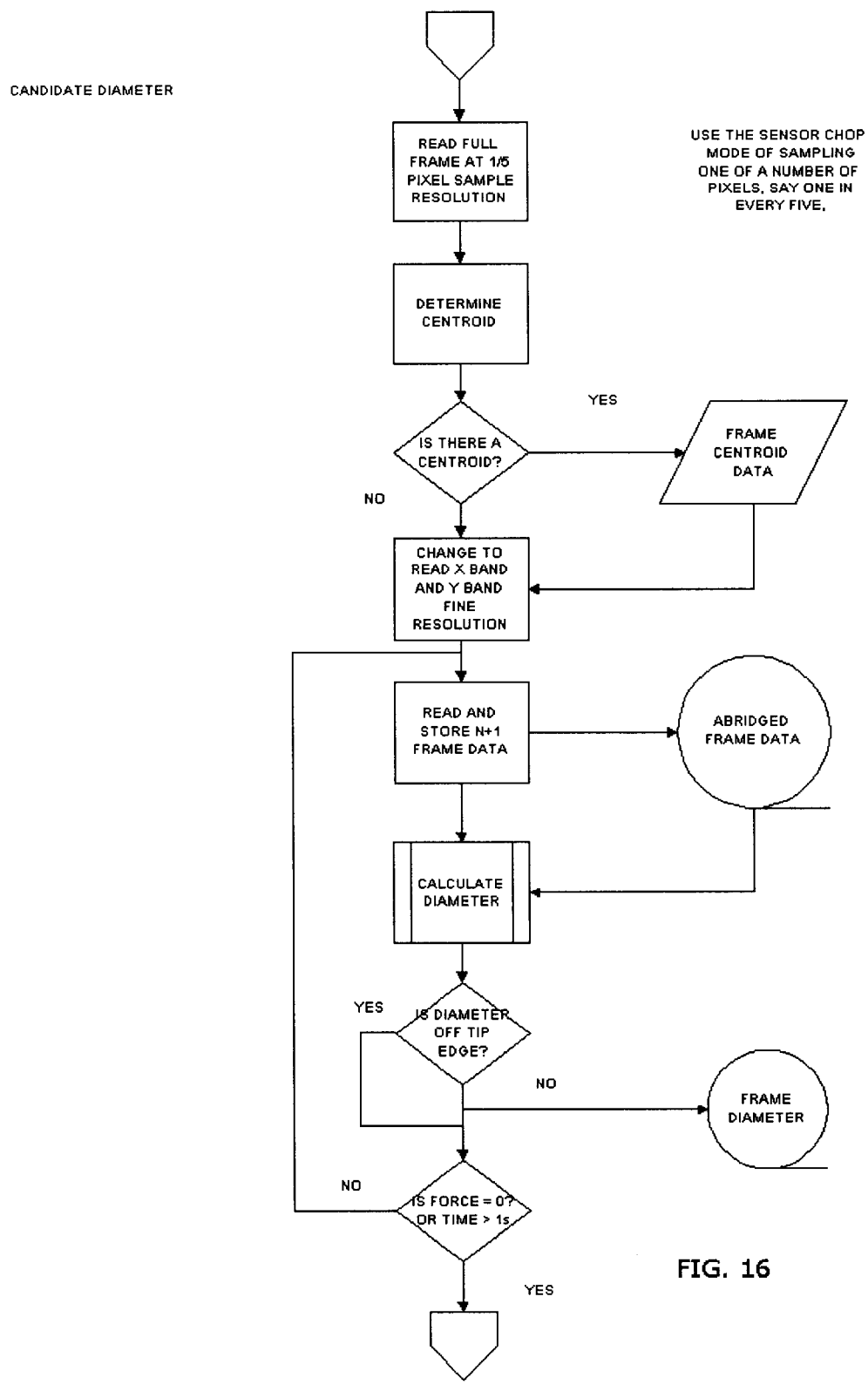

The "Candidate Diameter" process is shown in FIG. 16. This process may be used if the calculations are performed between the capture of frames or between capture of lines within frames.

Figure 17:
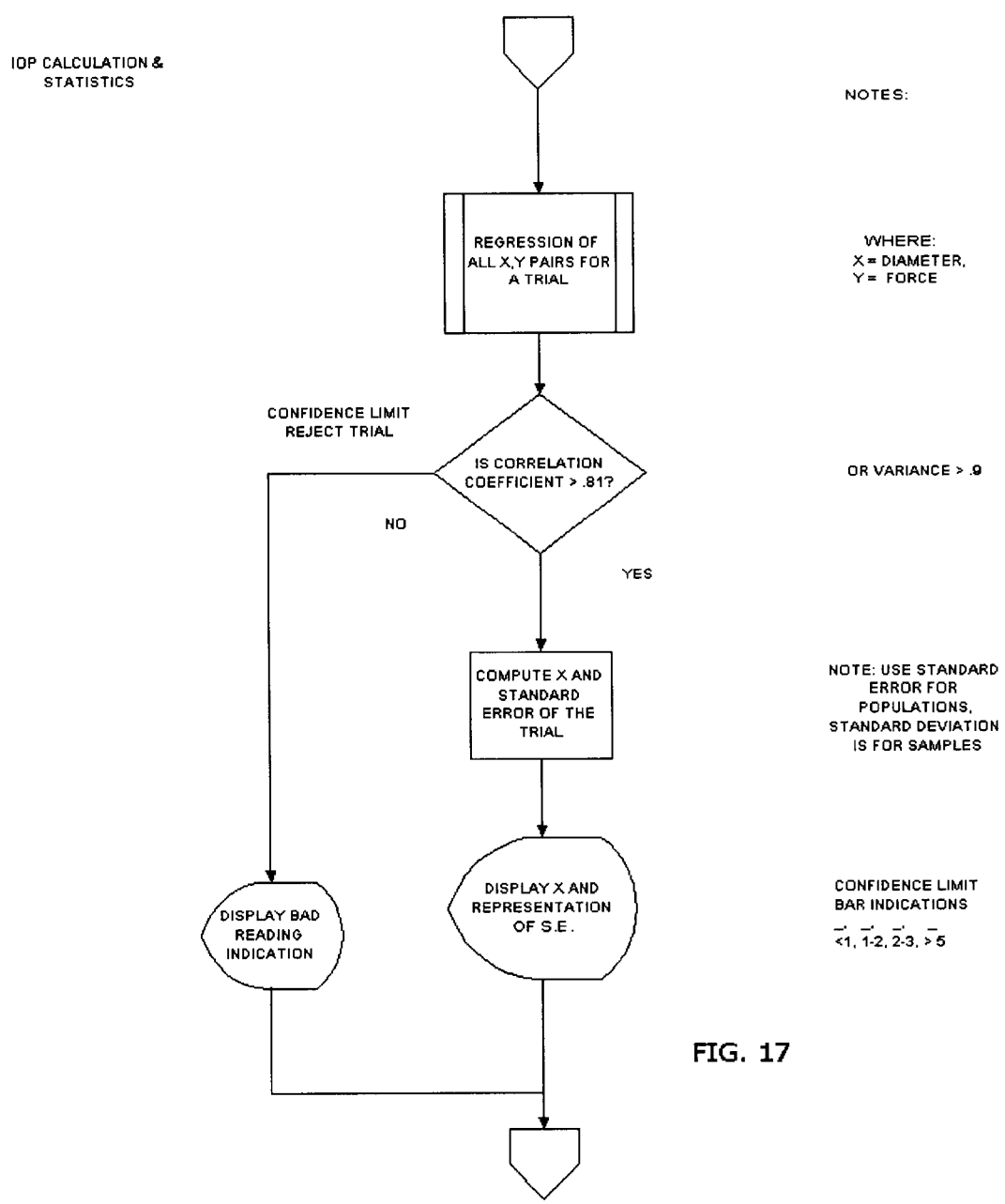
Figure 18:
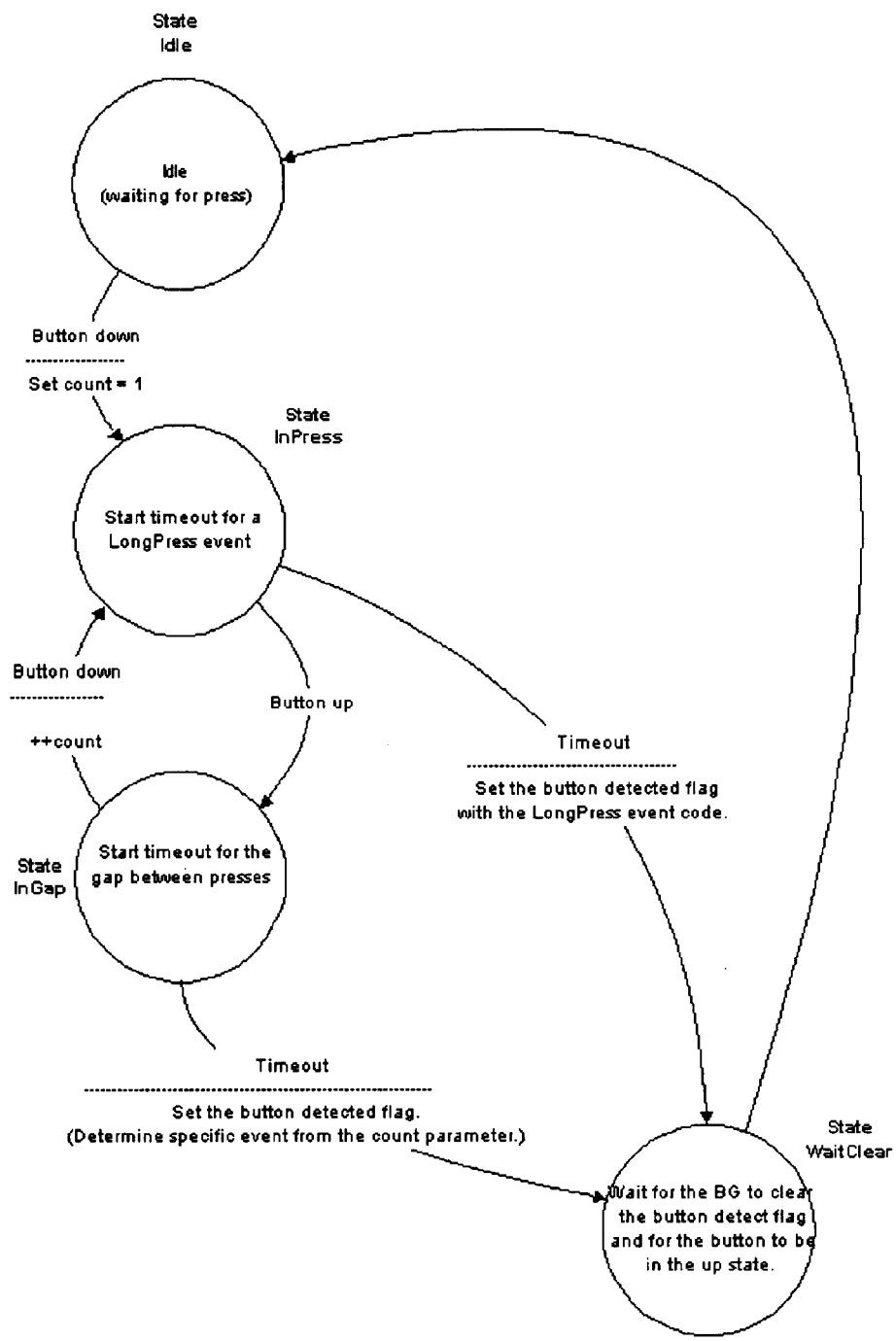
FIGS. 18–21 are state diagrams.
Figure 19:
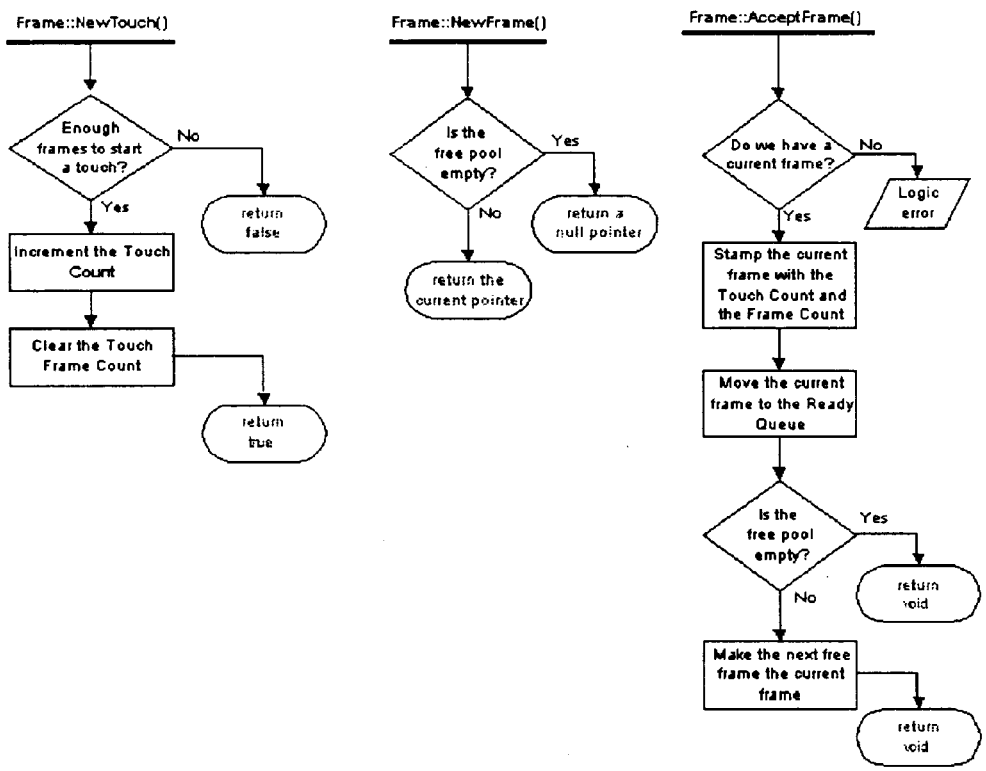
Figure 20:
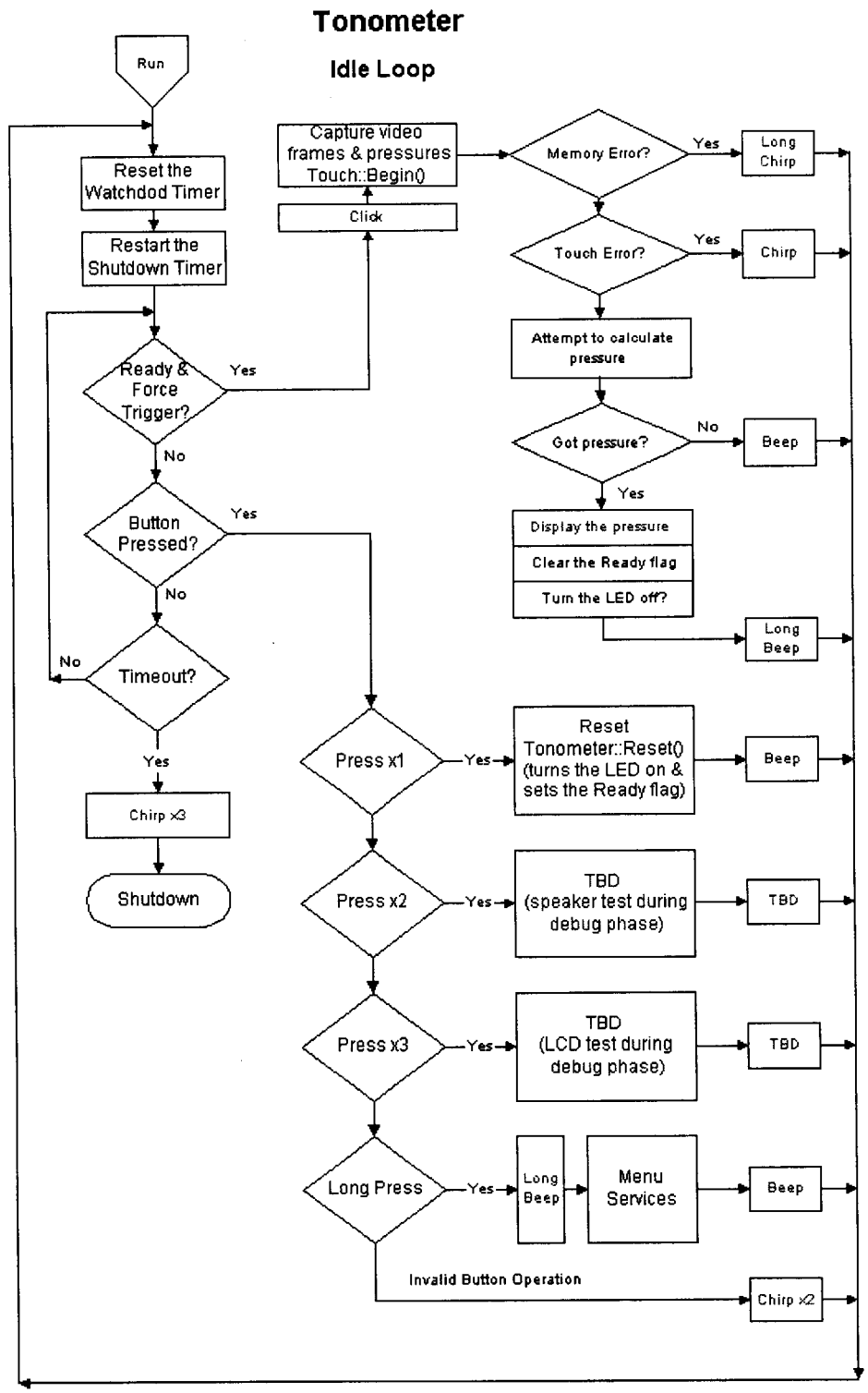
Figure 21:
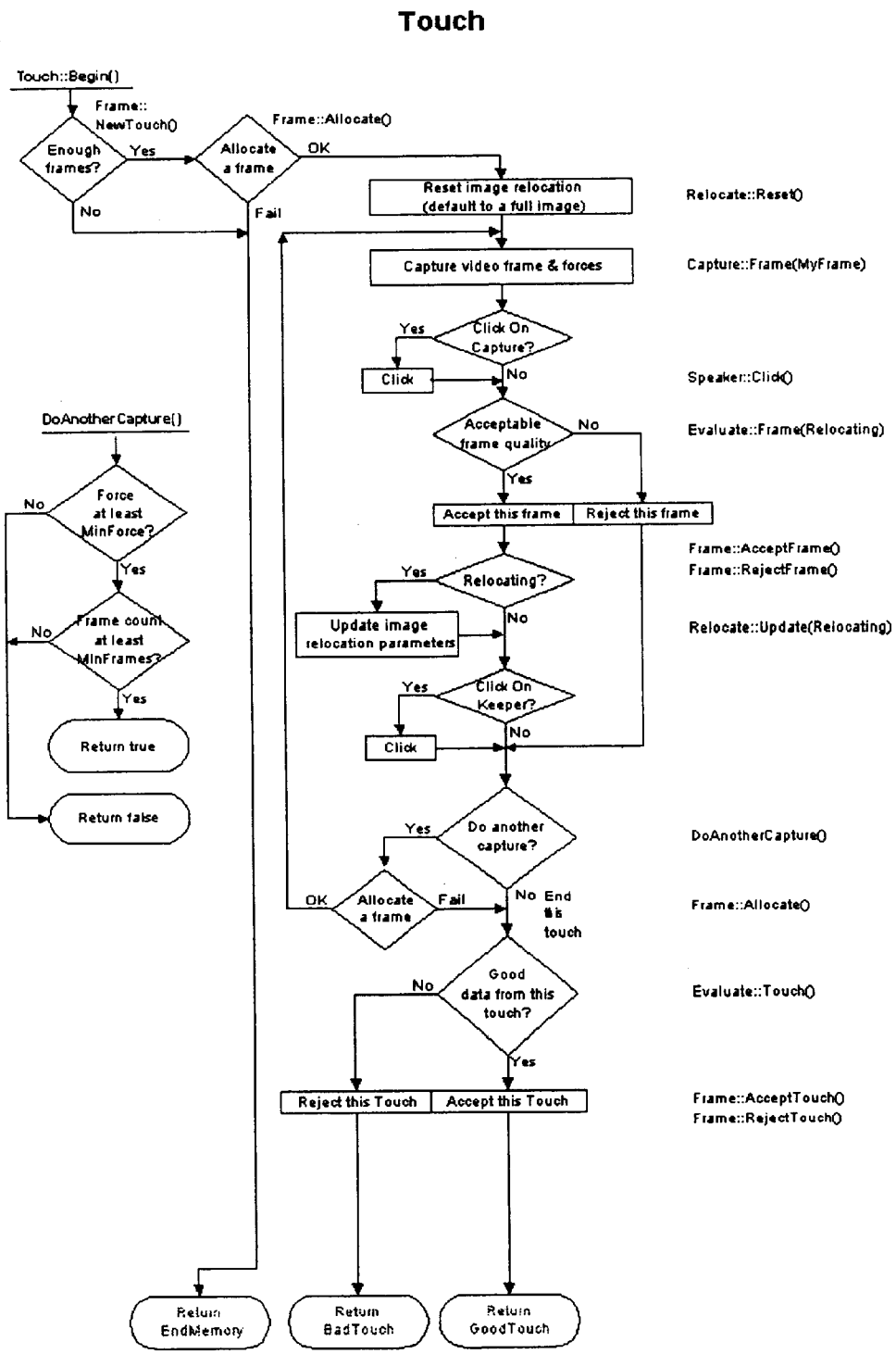

The "IOP Calculation and Statistics" process is shown in FIG. 17. This diagram is an expansion of the "IOP Calculation and Statistics" block shown in FIG. 15. This process determines the displayed IOP and the displayed symbol for statistical fit.

FIGS. 18–21 are state diagrams. The FIG. 18 "Class Button" diagram is the highest state level diagram for the tonometer. This diagram shows the relationship between the high-level tonometer states it contains. The FIG. 19, "Frame" diagram, shows some of the functions for the "Frame" class. The FIG. 20 "Tonometer" diagram shows the states for tonometer idle loop. The FIG. 21 "touch" diagram shows the states for a single "touch," or a single tonometer measurement.

Turning again to the disposable tip 12, it is first noted that the tip of the applanator 11 preferably is a 0.250 inch diameter fused glass bundle serving as an image conduit that protrudes forwardly from the apparatus approximately ¼ inch. A single use disposable tip or cover 12 is a two part device comprising a single sheet of one (1) mil thickness approximately ¾" diameter semi-transparent ethyl vinyl acetate (EVA) or other suitable film securely retained over the end of the applanator tip by a removable elastic rubber or neoprene O-ring such as with an $^{11}/_{32}$" OD×$^{7}/_{32}$" ID×$^{7}/_{32}$"×$^{1}/_{16}$ diameter wall. A stepped cavity tool as described below preferably is provided onto which the film and O-ring are disposed so that the tip of the applanator can be pressed into this tool to automatically wrap the film over the distal end 36 and seat the O-ring onto the periphery of the applanator 11.

Figure 22:
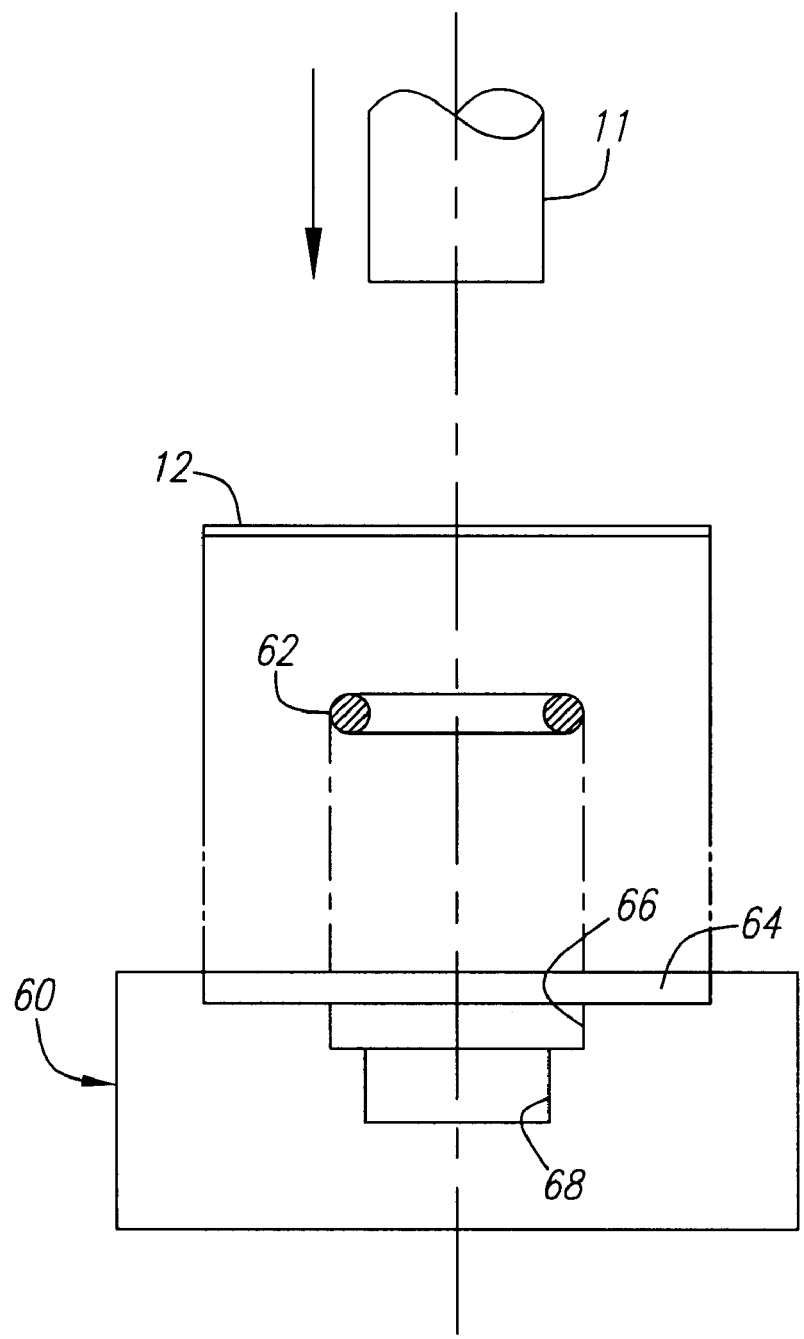
FIG. 22 illustrates the manner and device for applying a disposable tip.

FIG. 22 illustrates the manner in which the disposable tip is applied onto the distal end 36 of the applanator 11 using an assembly tool 60 and O-ring 62. The assembly tool can be formed of clear acrylic or any plastic machined or moldable material. The tool has an upper cavity 64 for receiving the film which results in the disposable tip 12. The tool 60 includes a next lower cavity 66 into which the O-ring is disposed or nested, and a lower or bottom cavity 68 for receiving the distal end of the applanator 11. The depth of the lower cavity should be deeper than the amount of exposed fiber optic array, to prevent damage to the piezoelectric element. As will be appreciated, the lower cavity 68 requires a slight clearance for the tip of the applanator, such as having a diameter of 0.300" for a 0.250 diameter applanator. In assembly, the O-ring is placed in the cavity 66 and the film placed in the film cavity 64. The distal tip of the applanator 11 is pushed into the assembly tool 60 and down into the lower cavity 68. This causes the film to wrap around the distal end of the applanator 11 forming the tip and causes the O-ring to slide part way up the applanator to secure the film/tip 12 thereto. In this manner, the disposable tip 12 can be simply and easily installed onto to the applanator for the purposes previously discussed.

While the preferred embodiments of the present invention have been illustrated and described in detail, certain modifications and alternatives will be apparent to those skilled in the art, and the present disclosure is intended to include such modifications and alternatives within the scope of the appended claims.

What is claimed is:

1. An applanation tonometer for measuring an intraocular pressure of an eye, comprising:
   an applanator for applanating a portion of an eye, wherein the applanator comprises a fiber optics array for transferring an image of a contact surface of an eye from a first end to a second end of the array within the tonometer;
   a force transducer operatively coupled to the applanator, wherein the force transducer is adapted to measure a force applied to the eye by the applanator as transferred by the array;
   an image sensor adapted to receive from the second end of the array an image of the applanated portion of the eye from the first end of the array and measure therefrom a geometrical property of the applanated portion of the eye; and
   a processing circuit communicatively coupled to the force transducer and the image sensor for acquiring data at a rate of approximately 20 Hz to 60 Hz, wherein the processing circuit is adapted to calculate an intraocular pressure of the eye using a measured force from the force transducer and a corresponding measured geometrical property from the image sensor.

2. The applanation tonometer of claim 1, wherein the geometrical property comprises an area of the applanated portion of the eye.

3. The applanation tonometer of claim 1, wherein the geometrical property comprises a diameter of the applanated portion of the eye.

4. The applanation tonometer of claim 1, further comprising a light source for illuminating from the second end of the array and through the array at least a portion of the eye.

5. The applanation tonometer of claim 1, wherein the applanator and image sensor are optically coupled with a lens system, the lens system adapted to focus an image of the applanated portion of the eye from the applanator to the image sensor.

6. The applanation tonometer of claim 1, wherein the force transducer comprises a piezoelectric element.

7. The applanation tonometer of claim 1, wherein the image sensor comprises one of a charge-coupled or CMOS device.

8. The applanation tonometer of claim 1, wherein the processing circuit is adapted to calculate an intraocular pressure of the eye using a plurality of measured forces from the force transducer and a corresponding plurality of measured geometrical properties from the image sensor.

9. The applanation tonometer of claim 1, further comprising a disposable tip adapted to cover at least part of the applanator where the applanator is designed to applanate an eye.

10. The applanation tonometer of claim 1, wherein the applanation tonometer is a portable, hand-held device, with an internal power supply.

11. The applanation tonometer of claim 1, further comprising a display for displaying the calculated intraocular pressure.

12. The applanation tonometer of claim 1, wherein the rate is approximately 30 Hz.

13. The applanation tonometer of claim 1, further including a disposable tip on the first end of the fiber optics array for engaging a contact surface of an eye, the disposable tip serving to diffuse reflected light.

14. An applanation tonometer comprising:

a fiber optics array adapted to applanate a portion of an eye at a distal end of the fiber optics array, whereby an image of the applanated portion of the eye is transmitted to a proximal end of the fiber optics array;

a first sensor optically coupled to the proximal end of the fiber optics array, the first sensor adapted to produce a first signal relating to the image of the applanated portion of the eye;

a second sensor adapted to produce a second signal relating to a force applied to the eye by the tonometer; and a processor communicatively coupled to the first and second sensors for receiving first and second signals, respectively, therefrom, a rate of approximately 20 Hz to 60 Hz, wherein the processor is adapted to calculate therefrom an intraocular pressure of the eye using the first and second signals.

15. The applanation tonometer of claim 14, wherein the first signal relates to the area of the image of the applanated portion of the eye.

16. The applanation tonometer of claim 14, wherein the first signal relates to the diameter of the image of the applanated portion of the eye.

17. The applanation tonometer of claim 14, further comprising a light source for illuminating through the array at least a portion of the eye.

18. The applanation tonometer of claim 14, wherein the proximal end of the fiber optic array is backlit.

19. The applanation tonometer of claim 14, wherein the proximal end of the fiber optics array is optically coupled to the firs sensor with a lens system, the lens system adapted to focus an image of the applanated portion of the eye from the proximal end of the fiber optics array to the first sensor.

20. The applanation tonometer of claim 14, wherein the processor is adapted to calculate an intraocular pressure of the eye using a plurality of corresponding first and second signals.

21. The applanation tonometer of claim 14, further comprising a light-diffusing disposable tip adapted to cover at least part of the fiber optics array where the fiber optics array is designed to applanate an eye.

22. The applanation tonometer of claim 14, wherein the distal end of fiber optics array has a matte finish.

23. A method of determining an intraocular pressure of an eye comprising:

applanating a portion of an eye, varying the applanation of the eye over a period of time;

acquiring a plurality of data points at distinct times, each data point comprising a first datum and a second datum, wherein the first datum relates to a force required to applanate the eye, and the second datum relates to a geometrical property of the applanated portion of the eye;

determining a slope of a line defined by the plurality of data points; and calculating the intraocular pressure using the slope and a predetermined relationship between said slope and intraocular pressure.

24. The method of claim 23, wherein the second datum relates to the area of the applanated portion of the eye.

25. The method of claim 23, wherein the second datum relates to the diameter of the applanated portion of the eye.

26. The method of claim 23, wherein the applanating step comprises using a fiber optics array to applanate the eye.

27. The method of claim 23, wherein the acquiring step is synchronous.

28. The method of claim 23, wherein the data points are acquired at the rate of approximately 20 Hz to 60 Hz.

29. A method of forming a disposable tip on a distal end of an applanator of a tonometer comprising the steps of disposing an elastic ring in an intermediate cavity of an assembly tool, disposing an optically light-diffusing film in an upper cavity of the assembly tool, and moving a distal end of the applanator of the tonometer axially into the assembly tool and down into a lower cavity to cause the film to wrap around the distal tip of the applanator and the elastic member to secure the ring thereto.

30. A method as in claim 29 wherein the elastic member is an O-ring.

31. An applanation tonometer for measuring an intraocular pressure of an eye, comprising:

an applanator for applanating a portion of an eye, the applanator comprising a fiber optics array for transferring an image of a contact surface of an eye from a first end to a second end of the array within the tonometer;

a force transducer operatively coupled to the applanator, wherein the force transducer is adapted to measure a force applied to the eye by the applanator as transferred by the array;

an image sensor adapted to receive an image of the applanated portion of the eye from the first end of the array and measure therefrom a geometrical property of the applanated portion of the eye;

a processing circuit communicatively coupled to the force sensor and the image sensor for acquiring data at a rate of approximately 20 Hz to 60 Hz, wherein the processing circuit is adapted to calculate an intraocular pressure of the eye using a measured force from the force transducer and a corresponding measured geometrical property from the image sensor; and a disposable tip for the distal end of the applanator comprising a small sheet of thin light-transmitting but optically light-diffusing film secured onto a distal end of the fiber optics array.

32. An applanation tonometer as in claim 31, wherein the data rate is approximately 30 Hz.

33. An applanation tonometer as in claim 31, wherein the disposable tip is secured at the distal end of the array via an elastic member.

* * * * *